(12) United States Patent
Jang

(10) Patent No.: US 8,562,665 B2
(45) Date of Patent: *Oct. 22, 2013

(54) TUBULAR STENT CONSISTS OF CHEVRON-SHAPE EXPANSION STRUTS AND CONTRALATERALLY ATTACHED DIAGONAL-CONNECTORS

(75) Inventor: G. David Jang, Redlands, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 3053 days.

This patent is subject to a terminal disclaimer.

(21) Appl. No.: 10/321,005

(22) Filed: Dec. 17, 2002

(65) Prior Publication Data

US 2003/0093144 A1 May 15, 2003

Related U.S. Application Data

(63) Continuation of application No. 09/839,287, filed on Apr. 20, 2001, now abandoned, which is a continuation of application No. 09/237,537, filed on Jan. 26, 1999, now Pat. No. 6,235,053.

(60) Provisional application No. 60/073,412, filed on Feb. 2, 1998.

(51) Int. Cl.
*A61F 2/06* (2013.01)

(52) U.S. Cl.
USPC ............. 623/1.15; 606/195; 606/198

(58) Field of Classification Search
USPC ............ 623/1.15, 1.16, 1.35; 606/191, 194, 606/195, 198
See application file for complete search history.

(56) References Cited

U.S. PATENT DOCUMENTS 2,836,181 A  5/1958  Tapp .............................. 128/334
3,015,492 A  10/1963 Jeckel ........................... 128/334
(Continued)

FOREIGN PATENT DOCUMENTS

DE  43 03 181 A1  8/1994
DE  296 08 037 U1  8/1996
(Continued)

OTHER PUBLICATIONS

Continued videotaped deposition of James E. Moore, Jr., PH.D., held at the offices of Kirkland & Ellis, LLP, 153 East 53$^{rd}$ Street, New York, New York, pursuant to adjournment, before Cary N. Bigelow, RPR, a Notary Public of the State of New York, dated Mar. 18, 2005, 8:33 a.m. (Case No. 03-027-SLR).

(Continued)

*Primary Examiner* — Vy Q Bui
(74) *Attorney, Agent, or Firm* — Vidas, Arrett & Steinkraus, P.A.

(57) ABSTRACT

A circumferentially connected stent in a non-expanded state with a longitudinal axis, includes a first expansion column strut pair having a first expansion strut, a second expansion strut with a joining strut. The first expansion column strut pair defines a chevron shaped slot, and a plurality of the first expansion strut pair forms a first expansion column. A second expansion column strut pair includes a first expansion strut, a second expansion strut and a joining strut. The second expansion column strut pair defines a chevron shaped slot, and a plurality of the second expansion strut pair forms a second expansion column. A first serial connecting strut column is formed of a plurality of first connecting struts, and the first connecting strut column couples the first expansion column to the second expansion column.

14 Claims, 4 Drawing Sheets

(56) References Cited

U.S. PATENT DOCUMENTS

| | | | | |
|---|---|---|---|---|
| 3,272,204 | A | 9/1966 | Artandi et al. | 128/334 |
| 3,490,975 | A | 1/1970 | Lightwood et al. | 156/167 |
| 3,509,883 | A | 5/1970 | Dibelius et al. | 128/348 |
| 3,526,228 | A | 9/1970 | Lyng | 128/334 |
| 3,562,820 | A | 2/1971 | Braun et al. | 3/1 |
| 3,635,215 | A | 1/1972 | Shea et al. | 128/130 |
| 3,771,526 | A | 11/1973 | Rudle | 128/334 |
| 3,868,956 | A | 3/1975 | Alfidi et al. | 128/345 |
| 3,993,078 | A | 11/1976 | Bergentz et al. | 128/334 |
| 4,078,167 | A | 3/1978 | Banas et al. | 219/121 |
| 4,127,761 | A | 11/1978 | Pauley et al. | 219/121 L |
| 4,130,904 | A | 12/1978 | Whalen | 3/1.4 |
| 4,140,126 | A | 2/1979 | Choudhury | 128/325 |
| 4,141,364 | A | 2/1979 | Schultze | 128/349 |
| 4,164,045 | A | 8/1979 | Bokros et al. | 3/1.4 |
| 4,214,587 | A | 7/1980 | Sakura, Jr. | 128/334 R |
| 4,300,244 | A | 11/1981 | Bokros | 3/1.4 |
| 4,313,231 | A | 2/1982 | Koyamada | 3/1.4 |
| 4,319,363 | A | 3/1982 | Ketharanathan | 3/1.4 |
| 4,425,908 | A | 1/1984 | Simon | 128/1 R |
| 4,441,215 | A | 4/1984 | Kaster | 3/1.4 |
| 4,470,407 | A | 9/1984 | Hussein | 128/6 |
| 4,501,264 | A | 2/1985 | Rockey | 128/1 R |
| 4,503,569 | A | 3/1985 | Dotter | 3/1.4 |
| 4,512,338 | A | 4/1985 | Balko et al. | 128/1 R |
| 4,535,770 | A | 8/1985 | Lemole | 128/327 |
| 4,550,447 | A | 11/1985 | Seiler, Jr. et al. | 623/1 |
| 4,553,545 | A | 11/1985 | Maass et al. | 128/341 |
| 4,560,374 | A | 12/1985 | Hammerslag | 604/49 |
| 4,580,568 | A | 4/1986 | Gianturco | 128/345 |
| 4,597,389 | A | 7/1986 | Ibrahim et al. | 128/328 |
| 4,647,416 | A | 3/1987 | Seiler, Jr. et al. | 264/118 |
| 4,649,922 | A | 3/1987 | Wiktor | 128/344 |
| 4,655,771 | A | 4/1987 | Wallsten | 623/1 |
| 4,655,776 | A | 4/1987 | Lesinski | 623/10 |
| 4,665,918 | A | 5/1987 | Garza et al. | 128/348 |
| 4,681,110 | A | 7/1987 | Wiktor | 128/348 |
| 4,693,721 | A | 9/1987 | Ducheyne | 623/16 |
| 4,733,665 | A | 3/1988 | Palmaz | 128/343 |
| 4,739,762 | A | 4/1988 | Palmaz | 128/343 |
| 4,740,207 | A | 4/1988 | Kreamer | 623/1 |
| 4,760,849 | A | 8/1988 | Kropf | 128/341 |
| 4,762,128 | A | 8/1988 | Rosenbluth | 128/343 |
| 4,768,507 | A | 9/1988 | Fischell et al. | 128/303 R |
| 4,769,029 | A | 9/1988 | Patel | 623/1 |
| 4,771,773 | A | 9/1988 | Kropf | 128/303 R |
| 4,776,337 | A | 10/1988 | Palmaz | 128/343 |
| 4,787,899 | A | 11/1988 | Lazarus | 623/1 |
| 4,795,458 | A | 1/1989 | Regan | 623/1 |
| 4,795,465 | A | 1/1989 | Marten | 623/9 |
| 4,800,882 | A | 1/1989 | Gianturco | 128/343 |
| 4,820,298 | A | 4/1989 | Leveen et al. | 623/1 |
| 4,830,003 | A | 5/1989 | Wolff et al. | 128/343 |
| 4,842,575 | A | 6/1989 | Hoffman, Jr. et al. | 600/36 |
| 4,848,343 | A | 7/1989 | Wallsten et al. | 128/343 |
| 4,851,009 | A | 7/1989 | Pinchuk | 623/66 |
| 4,856,516 | A | 8/1989 | Hillstead | 128/343 |
| 4,872,874 | A | 10/1989 | Taheri | 623/1 |
| 4,877,030 | A | 10/1989 | Beck et al. | 128/343 |
| 4,878,906 | A | 11/1989 | Lindemann et al. | 623/1 |
| 4,886,062 | A | 12/1989 | Wiktor | 128/343 |
| 4,913,141 | A | 4/1990 | Hillstead | 606/108 |
| 4,922,905 | A | 5/1990 | Strecker | 606/195 |
| 4,950,227 | A | 8/1990 | Savin et al. | 604/8 |
| 4,950,258 | A | 8/1990 | Kawai et al. | 604/281 |
| 4,994,071 | A | 2/1991 | MacGregor | 606/194 |
| 5,015,253 | A | 5/1991 | MacGregor | 621/1 |
| 5,019,090 | A | 5/1991 | Pinchuk | 606/194 |
| 5,035,706 | A | 7/1991 | Giantureo et al. | 606/198 |
| 5,037,392 | A | 8/1991 | Hillstead | 604/96 |
| 5,059,211 | A | 10/1991 | Stack et al. | 606/198 |
| 5,064,435 | A | 11/1991 | Porter | 623/12 |
| 5,092,877 | A | 3/1992 | Pinchuk | 623/1 |
| 5,102,417 | A | 4/1992 | Palmaz | 606/195 |
| 5,104,399 | A | 4/1992 | Lazarus | 623/1 |
| 5,104,404 | A | 4/1992 | Wolff | 623/1 |
| 5,108,417 | A | 4/1992 | Sawyer | 606/198 |
| 5,122,154 | A | 6/1992 | Rhodes | 606/198 |
| 5,133,732 | A | 7/1992 | Wiktor | 606/195 |
| 5,135,536 | A | 8/1992 | Hillstead | 606/195 |
| 5,139,480 | A | 8/1992 | Hickle et al. | 604/8 |
| 5,147,385 | A | 9/1992 | Beck et al. | 623/1 |
| 5,147,400 | A | 9/1992 | Kaplan et al. | 623/13 |
| 5,158,548 | A | 10/1992 | Lau et al. | 604/96 |
| 5,163,952 | A | 11/1992 | Froix | 623/1 |
| 5,195,984 | A | 3/1993 | Schatz | 606/195 |
| 5,197,978 | A | 3/1993 | Hess | 623/1 |
| 5,217,483 | A | 6/1993 | Tower | 606/198 |
| 5,226,913 | A | 7/1993 | Pinchuk | 623/1 |
| 5,282,823 | A | 2/1994 | Schwartz et al. | 606/198 |
| 5,282,824 | A | 2/1994 | Gianturco | 606/198 |
| 5,292,331 | A | 3/1994 | Boneau | 606/198 |
| 5,304,200 | A | 4/1994 | Spaulding | 606/198 |
| 5,312,430 | A | 5/1994 | Rosenbluth et al. | 606/192 |
| 5,314,472 | A | 5/1994 | Fontaine | 623/12 |
| 5,344,425 | A | 9/1994 | Sawyer | 606/198 |
| 5,354,308 | A | 10/1994 | Simon et al. | 606/198 |
| 5,383,892 | A | 1/1995 | Cardon et al. | 606/198 |
| 5,389,106 | A | 2/1995 | Tower | 606/198 |
| 5,405,377 | A | 4/1995 | Cragg | 623/1 |
| 5,449,373 | A | 9/1995 | Pinchasik et al. | 606/198 |
| 5,507,767 | A | 4/1996 | Maeda et al. | 606/198 |
| 5,527,354 | A | 6/1996 | Fontaine et al. | 623/1 |
| 5,545,210 | A | 8/1996 | Hess et al. | 623/1 |
| 5,549,663 | A | 8/1996 | Cottone, Jr. | 623/1 |
| 5,591,197 | A | 1/1997 | Orth et al. | 606/198 |
| 5,593,442 | A | 1/1997 | Klein | 623/12 |
| 5,607,442 | A | 3/1997 | Fischell et al. | 606/191 |
| 5,613,981 | A | 3/1997 | Boyle et al. | 606/198 |
| 5,653,727 | A | 8/1997 | Wiktor | 606/195 |
| 5,669,924 | A | 9/1997 | Shaknovich | 606/108 |
| 5,676,671 | A | 10/1997 | Inoue | 606/108 |
| 5,695,516 | A | 12/1997 | Fischell et al. | 606/198 |
| 5,697,971 | A | 12/1997 | Fischell et al. | 623/1 |
| 5,707,386 | A | 1/1998 | Schnepp-Pesch et al. | 606/194 |
| 5,713,949 | A | 2/1998 | Jayaraman | 623/1 |
| 5,716,393 | A | 2/1998 | Lindenberg et al. | |
| 5,718,713 | A | 2/1998 | Frantzen | 606/198 |
| 5,733,301 | A | 3/1998 | Forman | 606/192 |
| 5,733,303 | A | 3/1998 | Israel et al. | 606/198 |
| 5,735,871 | A | 4/1998 | Sgro | 606/198 |
| 5,735,893 | A | 4/1998 | Lau et al. | 623/1 |
| 5,741,327 | A | 4/1998 | Frantzen | 623/1 |
| 5,755,776 | A | 5/1998 | Al-Saadon | 623/1 |
| 5,755,781 | A | 5/1998 | Jayaraman | 623/1 |
| 5,759,192 | A | 6/1998 | Saunders | 606/194 |
| 5,772,864 | A | 6/1998 | Moller et al. | 205/73 |
| 5,776,161 | A | 7/1998 | Globerman | 606/194 |
| 5,776,181 | A | 7/1998 | Lee et al. | 623/1 |
| 5,776,183 | A | 7/1998 | Kanesaka et al. | 623/1 |
| 5,807,404 | A | 9/1998 | Richter | 623/1 |
| 5,810,767 | A | 9/1998 | Klein | 604/53 |
| 5,810,872 | A | 9/1998 | Kanesaka et al. | 606/198 |
| 5,824,043 | A | 10/1998 | Cottone, Jr. | 623/1 |
| 5,824,059 | A | 10/1998 | Wijay | 623/1 |
| 5,827,321 | A | 10/1998 | Roubin et al. | 606/195 |
| 5,836,951 | A | 11/1998 | Rosenbluth et al. | 606/108 |
| 5,836,964 | A | 11/1998 | Richter et al. | 606/194 |
| 5,843,120 | A | 12/1998 | Israel et al. | 606/198 |
| 5,843,172 | A | 12/1998 | Yan | 623/1 |
| 5,861,027 | A * | 1/1999 | Trapp | 623/1.15 |
| 5,876,449 | A * | 3/1999 | Starck et al. | 623/23.7 |
| 5,879,370 | A | 3/1999 | Fischell et al. | 606/198 |
| 5,895,406 | A | 4/1999 | Gray et al. | 606/198 |
| 5,897,588 | A | 4/1999 | Hull et al. | 623/1 |
| 5,902,317 | A | 5/1999 | Kleshinski et al. | 606/198 |
| 5,902,332 | A | 5/1999 | Schatz | 623/1 |
| 5,911,754 | A | 6/1999 | Kanesaka et al. | 623/1 |
| 5,913,895 | A | 6/1999 | Burpee et al. | 623/1 |
| 5,922,019 | A | 7/1999 | Hankh et al. | 623/1 |
| 5,922,020 | A | 7/1999 | Klein et al. | 623/1 |
| 5,922,021 | A | 7/1999 | Jang | 623/1 |
| 5,925,061 | A | 7/1999 | Ogi et al. | |
| 5,938,682 | A * | 8/1999 | Hojeibane et al. | 606/198 |

(56) References Cited

U.S. PATENT DOCUMENTS

| | | | |
|---|---|---|---|
| 5,939,227 A | 8/1999 | Smith | 430/5 |
| 5,948,016 A | 9/1999 | Jang | 623/1 |
| 5,953,743 A | 9/1999 | Jeddeloh | 711/158 |
| 5,954,743 A | 9/1999 | Jang | 606/198 |
| 5,964,798 A | 10/1999 | Imran | 623/1 |
| 5,968,093 A | 10/1999 | Kranz | 623/1 |
| 5,972,027 A | 10/1999 | Johnson | 623/1 |
| 5,980,553 A | 11/1999 | Gray et al. | 606/198 |
| 6,033,433 A | 3/2000 | Ehr et al. | 623/1.16 |
| 6,039,756 A | 3/2000 | Jang | 623/1 |
| 6,042,606 A | 3/2000 | Frantzen | 623/1 |
| 6,053,940 A | 4/2000 | Wijay | 623/1 |
| 6,066,169 A | 5/2000 | McGuinness | 623/1.16 |
| 6,106,548 A | 8/2000 | Roubin et al. | 623/1.15 |
| 6,113,627 A | 9/2000 | Jang | 623/1 |
| 6,117,165 A | 9/2000 | Becker | 623/1 |
| 6,123,721 A | 9/2000 | Jang | 623/1 |
| 6,129,755 A | 10/2000 | Mathis et al. | 623/1.15 |
| 6,152,957 A | 11/2000 | Jang | 623/1.37 |
| 6,156,052 A | 12/2000 | Richter et al. | 606/191 |
| 6,162,243 A | 12/2000 | Gray et al. | 623/1.11 |
| 6,168,621 B1 | 1/2001 | Vrba | |
| 6,179,868 B1 | 1/2001 | Burpee et al. | 623/1.17 |
| 6,183,506 B1 | 2/2001 | Penn et al. | 623/1.15 |
| 6,190,403 B1 | 2/2001 | Fischell et al. | 623/1 |
| 6,190,404 B1 | 2/2001 | Palmaz et al. | 623/1.15 |
| 6,190,406 B1 | 2/2001 | Duerig et al. | 623/1.2 |
| 6,193,744 B1 | 2/2001 | Ehr et al. | 623/1 |
| 6,193,747 B1 | 2/2001 | Von Oepen | 623/1.15 |
| 6,200,334 B1 | 3/2001 | Jang | 623/1.1 |
| 6,200,337 B1 | 3/2001 | Moriuchi et al. | 623/1.15 |
| 6,203,569 B1 | 3/2001 | Wijay | 623/1.15 |
| 6,206,911 B1 | 3/2001 | Milo | 623/1.15 |
| 6,206,915 B1 | 3/2001 | Fagan et al. | 623/1.42 |
| 6,206,916 B1 | 3/2001 | Furst | 623/1.46 |
| 6,217,608 B1 | 4/2001 | Penn et al. | 623/1.16 |
| 6,231,598 B1 | 5/2001 | Berry et al. | 623/1.15 |
| 6,235,053 B1 | 5/2001 | Jang | 623/1.15 |
| 6,241,760 B1 | 6/2001 | Jang | 623/1.12 |
| 6,251,134 B1 | 6/2001 | Alt et al. | 623/1.16 |
| 6,254,632 B1 | 7/2001 | Wu et al. | 623/1.15 |
| 6,258,121 B1 | 7/2001 | Yang et al. | 623/1.46 |
| 6,261,319 B1 | 7/2001 | Keveen et al. | 623/1.15 |
| 6,261,320 B1 | 7/2001 | Tam et al. | 623/1.15 |
| 6,270,524 B1 | 8/2001 | Kim | 623/1.15 |
| 6,273,908 B1 | 8/2001 | Ndondo-Lay | 623/1 |
| 6,273,911 B1 | 8/2001 | Cox et al. | 623/1.15 |
| 6,273,913 B1 | 8/2001 | Wright et al. | 623/1.42 |
| 6,280,413 B1 | 8/2001 | Clark et al. | 604/104 |
| 6,331,189 B1 * | 12/2001 | Wolinsky et al. | 623/1.15 |
| 6,348,065 B1 | 2/2002 | Brown et al. | 623/1.16 |
| 6,355,059 B1 | 3/2002 | Richter et al. | 623/1.17 |
| 6,379,381 B1 | 4/2002 | Hossainy et al. | 623/1.42 |
| 6,398,805 B1 | 6/2002 | Alt | 623/1.15 |
| 6,409,761 B1 | 6/2002 | Jang | 623/6.12 |
| 6,416,538 B1 | 7/2002 | Ley et al. | 623/1.15 |
| 6,423,090 B1 | 7/2002 | Hancock | 623/1.15 |
| 6,432,133 B1 | 8/2002 | Lau et al. | 623/1.15 |
| 6,443,982 B1 | 9/2002 | Israel et al. | 623/1.17 |
| 6,451,049 B2 | 9/2002 | Vallana et al. | 623/1.15 |
| 6,461,380 B1 | 10/2002 | Cox | 623/1.17 |
| 6,461,381 B2 | 10/2002 | Israel et al. | 623/1.17 |
| 6,464,720 B2 | 10/2002 | Boatman et al. | 623/1.15 |
| 6,464,722 B2 | 10/2002 | Israel et al. | 623/1.17 |
| 6,468,302 B2 | 10/2002 | Cox et al. | 623/1.15 |
| 6,471,720 B1 | 10/2002 | Ehr et al. | 623/1.15 |
| 6,475,236 B1 | 11/2002 | Roubin et al. | 623/1.15 |
| 6,478,816 B1 | 11/2002 | Kveen et al. | 623/1.15 |
| 6,485,508 B1 | 11/2002 | McGuinness | 623/1.15 |
| 6,602,281 B1 * | 8/2003 | Klein | 623/1.15 |
| 7,179,286 B2 | 2/2007 | Lenz | |
| 7,731,746 B2 | 6/2010 | Kveen et al. | |
| 7,780,719 B2 | 8/2010 | Killion et al. | |
| 7,905,912 B2 | 3/2011 | Ehr et al. | |
| 2001/0010013 A1 | 7/2001 | Cox et al. | 623/1.15 |
| 2001/0020183 A1 | 9/2001 | Jang | 623/1.15 |
| 2001/0035783 A1 | 11/2001 | Kanba | 327/202 |
| 2002/0038145 A1 | 3/2002 | Jang | 623/1.15 |
| 2002/0042647 A1 | 4/2002 | Jang | 623/1.15 |
| 2002/0045933 A1 | 4/2002 | Jang | 623/1.15 |
| 2002/0045934 A1 | 4/2002 | Jang | 623/1.15 |
| 2002/0045935 A1 | 4/2002 | Jang | 623/1.16 |
| 2002/0049493 A1 | 4/2002 | Jang | 623/1.16 |
| 2002/0058990 A1 | 5/2002 | Jang | 623/1.15 |
| 2002/0156524 A1 | 10/2002 | Ehr et al. | 623/1.15 |
| 2002/0161429 A1 | 10/2002 | Jang | 623/1.15 |
| 2002/0193870 A1 | 12/2002 | Jang | 623/1.16 |
| 2003/0028242 A1 | 2/2003 | Vallana et al. | 623/1.15 |
| 2003/0120335 A1 | 6/2003 | Ehr et al. | 623/1.15 |
| 2003/0144729 A1 | 7/2003 | Bicek et al. | |

FOREIGN PATENT DOCUMENTS

| | | |
|---|---|---|
| DE | 297 01 758 U1 | 5/1997 |
| DE | 297 02 671 U1 | 5/1997 |
| DE | 297 08 689 U1 | 8/1997 |
| DE | 297 08 879 U1 | 9/1997 |
| EP | 0 183 372 A1 | 6/1986 |
| EP | 0 364 787 A1 | 4/1990 |
| EP | 0 364 787 B1 | 4/1990 |
| EP | 0 335 341 B1 | 4/1992 |
| EP | 0 540 290 A2 | 5/1993 |
| EP | 0 606 165 A1 | 1/1994 |
| EP | 0 587 197 A1 | 3/1994 |
| EP | 0 679 372 A2 | 11/1995 |
| EP | 0 709 067 A2 | 1/1996 |
| EP | 0 734 698 A2 | 2/1996 |
| EP | 0 821 920 A1 | 2/1998 |
| EP | 0 875 215 A1 | 11/1998 |
| EP | 0 950 386 A2 | 10/1999 |
| EP | 0 980 694 A2 | 2/2000 |
| FR | 2 785 174 A1 | 5/2000 |
| WO | WO 94/17754 A1 | 8/1994 |
| WO | WO 96/03029 A1 | 2/1996 |
| WO | WO 96/03092 A1 | 2/1996 |
| WO | WO 96/26689 A1 | 9/1996 |
| WO | WO 97/14375 A1 | 4/1997 |
| WO | WO 97/25937 A1 | 7/1997 |
| WO | WO 97/26840 A1 | 7/1997 |
| WO | WO 97/32543 A1 | 9/1997 |
| WO | WO 97/32544 A1 | 9/1997 |
| WO | WO 97/33534 A1 | 9/1997 |
| WO | WO 97/40780 A1 | 11/1997 |
| WO | WO 97/40781 A1 | 11/1997 |
| WO | WO 97/40782 A1 | 11/1997 |
| WO | WO 97/40783 A2 | 11/1997 |
| WO | WO 97/40784 A1 | 11/1997 |
| WO | WO 98/20810 A1 | 5/1998 |
| WO | WO 98/23228 A1 | 6/1998 |
| WO | WO 98/36784 A1 | 8/1998 |
| WO | WO 98/40035 A1 | 9/1998 |
| WO | WO 98/42278 A1 | 10/1998 |
| WO | WO 99/01088 A1 | 1/1999 |
| WO | WO 99/15107 A1 | 4/1999 |
| WO | WO 99/15108 A2 | 4/1999 |
| WO | WO 99/23977 A1 | 5/1999 |
| WO | WO 99/38457 A1 | 8/1999 |
| WO | WO 99/40876 A2 | 8/1999 |
| WO | WO 99/55253 A1 | 11/1999 |
| WO | WO 00/03661 A1 | 1/2000 |
| WO | WO 00/06051 | 2/2000 |
| WO | 00/15145 A1 | 3/2000 |
| WO | WO 00/13611 A1 | 3/2000 |
| WO | WO 00/30563 A1 | 6/2000 |
| WO | WO 00/62710 A1 | 10/2000 |
| WO | WO 01/26584 A1 | 4/2001 |
| WO | WO 01/66036 A2 | 9/2001 |
| WO | WO 01/91918 A1 | 12/2001 |
| WO | WO 01/93781 A2 | 12/2001 |
| WO | WO 02/24112 A2 | 3/2002 |

(56) References Cited

FOREIGN PATENT DOCUMENTS

OTHER PUBLICATIONS

Videotaped deposition of James E. Moore, Jr., PH.D., held at the offices of Kirkland & Ellis, LLP, 153 East 53rd Street, New York, New York, pursuant to notice, before Cary N. Bigelow, RPR, a Notary Public of the State of New York, dated Mar. 17, 2005, 9:32 a.m. (Case No. 03-027-SLR).
Corrected Rebuttal Expert Report of Professor James E. Moore Jr., PH.D., dated Mar. 14, 2005 (Case No. 03-027-SLR).
Corrected Expert Report of Professor James E. Moore Jr., Ph.D., dated Feb. 11, 2005 (Case No. 03-027-SLR).
Opening Expert Report of Nigel Buller, B.SC, M.B., F.R.C.P. regarding Validity of the Jang Patent (Case No. 03-027-SLR).
Deposition of Nigel Buller, held at the offices of Patterson, Belknap, Webb & Tyler, 1133 Avenue of the Americas, New York, New York, before Laurie A. Collins, a Registered Professional Reporter and Notary Public of the State of New York, dated Mar. 2, 2005, 9:32 a.m. (Case No. 03-027-SLR).
Continued deposition of Nigel Buller, held at the offices of Patterson, Belknap, Webb & Tyler, 1133 Avenue of the Americas, New York, New York, before Laurie A. Collins, a Registered Professional Reporter and Notary Public of the State of New York, dated Mar. 3, 2005, 8:45 a.m. (Case No. 03-027-SLR).
Rebuttal Expert Report of Nigel Buller, B.SC., M.B., F.R.C.P., dated Feb. 25, 2005 (Case No. 03-027-SLR).
Videotaped Deposition of the David Morre Parks, Ph.D., a witness called on behalf of the Defendants, pursuant to the Federal Rules of Civil Procedure, before Judith McGovern Williams, Certified Shorthand Reporter No. 130993, Registered Professional Reporter, Certified Realtime Reporter, and Notary Public in and for the Commonwealth of Massachusetts, at the Hyatt Regency, 575 Memorial Drive, Cambridge, Massachusetts, on Monday, Mar. 21, 2005, commencing at 9:32 a.m. (Case No. 03-027-SLR).
Opening Expert Report of David M. Parks, PH.D. Regarding Validity of the Jang Patent, dated Jan. 28, 2005 (Case No. 03-027-SLR).
Rebuttal Expert Report of David M. Parks, PH.D., dated Feb. 25, 2005 (Case No. 03-027-SLR).
BSC's Opposition to Cordis' Motion for Summary Judgment of Noninfringement of Claim 36 of the Jang '021 Patent, dated Apr. 14, 2005 (Case No. 03-027-SLR).
Redacted Version—Publicly Filed BSC's Opposition to Cordis' Motion for Summary Judgment of Noninfringement of Claim 36 of the Jang '021 Patent, dated Apr. 14, 2005 (Case No. 03-027-SLR).
Redacted Public Version: Opening Brief in Support of Cordis' Motion for Summary Judgement of Noninfringement of Claim 36 of the Jang '021 Patent, dated Mar. 31, 2005 (Case No. 03-027-SLR).
Opening Brief in Support of Cordis' Motion for Summary Judgment of Noninfringement of Claim 36 of the Jang '021 Patent, dated Mar. 24, 2005 (Case No. 03-027-SLR).
Reply Brief in Support of Cordis' Motion for Summary Judgment of Noninfringement of the Jang '021 Patent, dated Apr. 21, 2005 (Case No. 03-027-SLR).
Order, dated Jun. 3, 2005 (Case No. 03-027-SLR).
Jury Verdict, dated Jul. 1, 2005 (Case No. 03-027-SLR and Case No. 03-283-SLR).
Jury Trial—vol. H, BSC v. Cordis & J&J, CA #03-27 & 03-283 (SLR), dated Friday, Jul. 1, 2005, pp. 1816-1857 and Index pp. 1-7.
Jury Trial—vol. A, BSC v. Cordis & J&J, CA #03-27 & 03-283 (SLR), dated Tuesday, Jun. 21, 2005, pp. 1-107 and Index pp. 1-12.
Jury Trial—vol. B, BSC v. Cordis & J&J, CA #03-27 & 03-283 (SLR), dated Wednesday, Jun. 22, 2005, pp. 108-407 and Index pp. 1-32.
Jury Trial—vol. C, BSC v. Cordis & J&J, CA #03-27 & 03-283 (SLR), dated Thursday, Jun. 23, 2005, pp. 408-691 and Index pp. 1-29.
Jury Trial—vol. D, BSC v. Cordis & J&J, CA #03-27 & 03-283 (SLR), dated Friday, Jun. 24, 2005, pp. 693-930 and Index pp. 1-23.
Jury Trial—vol. E, BSC v. Cordis & J&J, CA #03-27 & 03-283 (SLR), dated Jun. 28, 2005, pp. 931-1223.
Under Seal—vol. EE, BSC v. Cordis & J&J, CA #03-27 & 03-283 (SLR), dated Tuesday Jun. 28, 2005, pp. 1-61and Index pp. 1-8.
Jury Trial—vol. F, BSC v. Cordis & J&J, CA #03-27 & 03-283 (SLR), dated Wednesday, Jun. 29, 2005, pp. 1224-1537 and Index pp. 1-32.
Jury Trial—vol. G, BSC v. Cordis & J&J, CA #03-27 & 03-283 (SLR), dated Thursday, Jun. 30, 2005, pp. 1538-1815 and Index pp. 1-30.
*Manufacturing Processes for Engineering Materials*, by Serope Kalpakjian, Illinois Institute of Technology, Addison-Wesley Publishing Company, pp. 340.
A View of Vascular Stents, by Richard A. Schatz, MD, From the Arizona Heart Institute Foundation, Phoenix ,Arizona, *Circulation*, vol. 79 No. 2, Feb. 1989, pp. 445-457.
*The Self-Expanding Mesh Stents*, by Ulrich Sigwart, Section IV, Chapter 29, pp. 605-610.
Improved Dilation Catheter Balloons, by Stanley B. Levy, Ph.D. *Journal of Clinical Engineering*, vol. 11, No. 4, Jul.-Aug. 1988, pp. 291-296.
Technical Note Entitled Modifications of Gianturco Expandable Wire Stents, by Barry T. Uchida et al., *AJR* vol. 150, May 1988, pp. 1185-1187.
Brochure from Cook Incorporated regarding Gianturaco-Rosch Biliary Z-Stents™.
Expandable Biliary Endoprosthesis: An Experimental Study, by Carrasco et al., *AJR*, vol. 145, Dec. 1985, pp. 1279-1282.
U.S. Appl. No. 09/999,279, filed Nov. 30, 2001, Jansen et al.
U.S. Appl. No. 10/297,372, filed Dec. 5, 2002, Jang.
U.S. Appl. No. 10/321,005, filed Dec. 17, 2002, Jang.
U.S. Appl. No. 60/073,412, filed Feb. 2, 1998, Jang.
U.S. Appl. No. 60/073,509, filed Feb. 3, 1998, Jang.
U.S. Appl. No. 60/234,614, filed Sep. 22, 2000, Jang.
U.S. Appl. No. 60/235,115, filed Sep. 25, 2000, Jang.
U.S. Appl. No. 60/235,164, filed Sep. 23, 2000, Jang.
U.S. Appl. No. 60/017,484, filed Apr. 26, 1996, Jang.
U.S. Appl. No. 09/574,077, filed May 18, 2000, Jang.
U.S. Appl. No. 60/235,167, filed Sep. 23, 2000, Jang.
U.S. Appl. No. 60/235,180, filed Sep. 25, 2000, Jang.
U.S. Appl. No. 08/845,734, filed Apr. 25, 1997, Jang.
Tracheobronchial Tree: Expandable Metallic Stents Used in Experimental and Clinical Applications, Work in Progress, by Wallace et al., *Radiology*, Feb. 1986, pp. 309-312.
Brochure Entitled *AVE MICRO STENT*™, Instructions for Use, by Applied Vascular Engineering, Inc., pp. 1-15.
Brochure Entitled *MICRO STENT*™, by Applied Vascular Engineering, Inc.
Japanese Infringement Search on Articulated Expandable Stents, Dated Jul. 12, 1995.
*Engineering Fluid Mechanics*, Third Edition, John A. Roberson and Clayton T. Crowe, pp. 94 and pp. 414-421.
*Cambridge Dictionary of Science and Technology*, Cambridge University Press p. 128.
Beyer et al., "The BeStent: The Parallel-Serial Jong Stents", *Handbook of Coronary Stents*, Second Edition, pp. 158-171 & pp. 229-234 (1998).
Beyer et al., "Newer Stents: Materials and Designs", *IAGS Proceedings*, 9 (5): 363-371 (Jun. 1977).
Roguin et al., "Acute and 30-Day Results of the Serpentine Balloon Expandable Stent Implantation in Simple and Complex Coronary Arterial Narrowings", *The American Journal of Cardiology*, 80:1155-1162 (Nov. 1997).
Roguin et al., "Be-Stent the Serpentine Balloon Expandable Stent: Review of Mechanical Properties and Clinical Experience", *Artif Organs*, 22(3): 243-249 (Mar. 1998).
Brochure Entitled Sorin Biomedica "CARBOSTENT™".

* cited by examiner

TUBULAR STENT CONSISTS OF CHEVRON-SHAPE EXPANSION STRUTS AND CONTRALATERALLY ATTACHED DIAGONAL-CONNECTORS

CROSS REFERENCE TO RELATED APPLICATIONS

This application is a continuation application of U.S. application Ser. No. 09/839,287, filed Apr. 20, 2001 now abandoned; which is a continuation application of U.S. application Ser. No. 09/237,537, filed Jan. 26, 1999, now U.S. Pat. No. 6,235,053 B1; which claims priority to provisional U.S. Application No. 60/073,412, filed Feb. 2, 1998, the contents of all of which are incorporated herein in their entirety by reference.

BACKGROUND OF THE INVENTION

1. Field of the Invention

This invention relates to intravascular stents, and more particularly to an intravascular stent which provides easy introduction through tortuous sections of vessels.

2. Description of the Related Art

Angioplasty, either coronary or general vascular, has advanced to become the most effective means for revascularization of stenosed vessels. In the early 1980's, angioplasty first became available for clinical practice in the coronary artery, and has since proven an effective alternative to conventional bypass graft surgery. Balloon catheter dependent angioplasty has consistently proven to be the most reliable and practical interventional procedure. Other ancillary technologies such as laser based treatment, or directional or rotational atherectomy, have proven to be either of limited effectiveness or dependent on balloon angioplasty for completion of the intended procedure. Restenosis following balloon-based angioplasty is the most serious drawback and is especially prevalent in the coronary artery system.

Many regimens have been designed to combat restenosis, with limited success, including laser based treatment and directional or rotational atherectomy. Intravascular stenting, however, noticeably reduces the restenosis rate following angioplasty procedures. The procedure for intravascular stent placement typically involves pre-dilation of the target vessel using balloon angioplasty, followed by deployment of the stent, and expansion of the stent such that the dilated vessel walls are supported from the inside.

The intravascular stent functions as scaffolding for the lumen of a vessel. The scaffolding of the vessel walls by the stent serve to: (a) prevent elastic recoil of the dilated vessel wall, (b) eliminate residual stenosis of the vessel, a common occurrence in balloon angioplasty procedures, (c) maintain the diameter of the stented vessel segment slightly larger than the native unobstructed vessel segments proximal and distal the stented segment, and (d) as indicated by the latest clinical data, lower the restenosis rate. Following an angioplasty procedure, the restenosis rate of stented vessels has proven significantly lower than for not stented or otherwise treated vessels; treatments include drug therapy and other methods mentioned previously.

Another benefit of vessel stenting is the potential reduction of emergency bypass surgery arising from angioplasty procedures. Stenting has proven to be effective in some cases for treating impending closure of a vessel during angioplasty. Stenting can also control and stabilize an unstable local intimal tear of a vessel caused by normal conduct during an angioplasty procedure. In some cases, an incomplete or less than optimal dilatation of a vessel lesion with balloon angioplasty can successfully be opened up with a stent implant.

Early in its development, the practice of stenting, especially in coronary arteries, had serious anticoagulation problems. However, anticoagulation techniques have since been developed and are becoming simpler and more effective. Better and easier to use regimens are continuously being introduced, including simple outpatient anticoagulation treatments, resulting in reduced hospital stays for stent patients.

An example of a conventional stent patent is U.S. Pat. No. 5,102,417 (hereafter the Palmaz Patent). The stent described in the Palmaz Patent consists of a series of elongated tubular members having a plurality of slots disposed substantially parallel to the longitudinal axis of the tubular members. The tubular members are connected by at least one flexible connector member.

The unexpanded tubular members of the Palmaz Patent are overly rigid so that practical application is limited to short lengths. Even with implementation of the Multi-link design with flexible connector members connecting a series of tubular members, longer stents can not navigate tortuous blood vessels. Furthermore, the rigidity of the unexpanded stent increases the risk of damaging vessels during insertion. Foreshortening of the stent during insertion complicates accurate placement of the stent and reduces the area that can be covered by the expanded stent. There is, further, no method of programming the stent diameter along its longitudinal axis to achieve a tapered expanded stent and no method of re-enforcement of stent ends or other regions is provided for.

Another example of a conventional stent patent is WO 96/03092, the Brun patent. The stent described in the Brun patent is formed of a tube having a patterned shape, which has first and second meander patterns. The even and odd first meander patterns are 180 degrees out of phase, with the odd patterns occurring between every two even patterns. The second meander patterns run perpendicular to the first meander patterns, along the axis of the tube.

Adjacent first meander patterns are connected by second meander patterns to form a generally uniform distributed pattern. The symmetrical arrangement with first and second meander patterns having sharp right angled bends allows for catching and snagging on the vessel wall during delivery. Furthermore, the large convolutions in the second meander pattern are not fully straightened out during expansion reducing rigidity and structural strength of the expanded stent. There is, further, no method of programming the stent diameter along its longitudinal axis to achieve a tapering stent design, and no method of re-enforcement of stent ends or other regions is provided for.

These and other conventional stent designs suffer in varying degrees from a variety of drawbacks including: (a) inability to negotiate bends in vessels due to columnar rigidity of the unexpanded stent, (b) lack of axio-lateral strength of the unexpanded stent, (c) significant foreshortening of the stent during expansion, (d) limited stent length, (e) even expanded stent diameter, (f) poor crimping characteristics, (g) rough surface modulation of the unexpanded stent, (h) poor vessel coverage and tissue prolapse, (i) rough vessel friction by un-connected strut tulips, and uneven stent expansion.

There is a need for a stent with sufficient longitudinal flexibility in the unexpanded state to allow for navigation through tortuous vessels. There is a further need for a stent that is structurally strong in the unexpanded state such that risk of damage or distortion during delivery is minimal. A further need exists for a stent that maintains substantially the same longitudinal length during expansion to allow greater coverage at the target site and simplify proper placement of the stent. Yet a further need exists for a stent design with sufficient longitudinal flexibility that long stents of up to 100 mm can be safely delivered through tortuous vessels. There is a need for a stent that is configured to expand to variable diameters along its length, such that a taper can be achieved in the expanded stent to match the natural taper of the target vessel. A need exists for a stent, which has better crimping qualities, increased axio-lateral and radial strength with low metal fraction, improved surface modulations with no strut tulips, full vessel coverage without tissue prolapse, flexible during delivery but transforms into a unitized rigidity, low profile during delivery, and high expansion ratio with minimal foreshortening.

SUMMARY OF THE INVENTION

Accordingly an object of the present invention is to provide a scaffold for an interior lumen of a vessel.

Another object of the invention is to provide a stent, which prevents recoil of the vessel following angioplasty.

A further object of the invention is to provide a stent that maintains a larger vessel lumen compared to the results obtained only with balloon angioplasty.

Yet another object of the invention is to provide a stent that reduces foreshortening of a stent length when expanded.

Another object of the invention is to provide a stent with increased flexibility when delivered to a selected site in a vessel.

A further object of the invention is to provide a stent with a low profile when crimped over a delivery balloon of a stent assembly.

Yet a further object of the invention is to provide a stent with reduced tuliping of a stent frame.

Another object of the invention is to provide a chain mesh stent that reduces vessel "hang up" in a tortuous vessel or a vessel with curvature.

A further object of the invention is to provide a chain mesh stent that increases radial and axio-lateral strength of the expanded stent.

These and other objectives of the invention are achieved in a stent designed in non-expanded state. The stent of present invention is a 3-dimensional object with a generally tubular geometry, which includes inner and outer surface, inner and outer diameter, an internal tubular lumen, a wall thickness and a prescribed length. To describe the design geometry of the stent of present invention, 2-dimensional cut-open illustrations of the stent are used extensively in this application. Although description of frame configurations of the stent is according to the 2-dimensional cut-open drawings, the real stent of present invention is a 3-dimensional tubular object designed to function as scaffolding device inside a blood vessel or inside an anatomic tubular structure of any kind in which the stent can be implanted.

A first expansion column includes of a plurality of first expansion strut pairs of chevron-shape in upright position. A first expansion strut pair includes a first expansion strut of generally a chevron-shape, which has a stair-step configuration at the center and is dissimilar to a second expansion strut configuration, adjacent to a second expansion strut of generally a chevron-shape. A first joining strut couples the first and second expansion struts of chevron-shape at a distal end of a first expansion strut pair to form a closed loop. When a first expansion strut pair is joined by a first joining strut to form a closed loop, a chevron-shaped slot is formed inside the first expansion strut pair, with a narrower slot width in the distal half, and a wider slot width in the proximal half due to the dissimilar chevron-shapes of the first and second first expansion struts of a first expansion strut pair. A second expansion strut pair includes a third expansion strut of chevron-shape, which has a stair-step configuration at the center and is dissimilar to a second expansion strut configuration, adjacent to the second expansion strut of chevron-shape. A second joining strut couples the second and third expansion struts at a proximal end of the second expansion strut pair to form a closed loop. When a second expansion strut pair is joined by a second joining strut to form a closed loop, a chevron-shaped slot is formed inside the second expansion strut pair, with a narrower slot width in the proximal half and a wider slot width in the distal half, due to the dissimilar chevron-shapes of the second and third expansion struts of a second expansion strut pair. A third expansion strut pair includes a fourth expansion strut of chevron-shape adjacent to the third expansion strut of chevron-shape, which has a stair-step configuration at the center and is dissimilar to a fourth expansion strut configuration. A third joining strut couples the third and fourth expansion struts at a distal end of the third expansion strut pair to form a closed loop. When a third expansion strut pair is joined by a third joining strut to form a closed loop, a chevron-shaped slot is formed inside the third expansion strut pair, with a narrower slot width in the distal half and a wider slot width in the proximal half, due to the dissimilar chevron-shapes of the third and fourth expansion struts of a third expansion strut pair. A fourth expansion strut pair includes a fifth expansion strut of chevron-shape, which has a stair-step configuration at the center and is dissimilar to a fourth expansion strut configuration adjacent to a fourth expansion strut of chevron-shape. A fourth joining strut couples the fourth and fifth expansion struts at a proximal end of the fourth expansion strut pair. When a fourth expansion strut pair is joined by a fourth joining strut to form a closed loop, a chevron-shaped slot is formed inside the fourth expansion strut pair, with a narrower slot width in the proximal half and a wider slot width in the distal half, due to the dissimilar chevron-shapes of the fourth and fifth expansion struts of a fourth expansion strut pair. These expansion strut pairs of two dissimilar chevron-shape coupled by a joining struts to form a closed loop in an alternating proximal or distal end of the expansion strut pairs can be repeated to make the prescribed number of continues chain of expansion strut pairs around the circumference in an unbroken fashion in the stent of present invention. A set of two consecutive chevron-shaped expansion strut pairs in an unbroken sequence is called expansion strut cycles. In this application, the illustrations contain six (6) chevron-shaped expansion strut pair cycles or twelve (12) chevron-shaped expansion strut pairs in a first expansion column in the 2-dimensional cut-open drawings. However, the number of chevron-shaped expansion strut pair or expansion strut pair cycle in a first expansion column can variably be changed according to the application requirements of the specific stent of present invention made. The variation of the number of expansion strut pair or expansion pair cycle in a first expansion column is within the scope of a tubular stent of present invention.

Although the illustrations in this application shows only a neutrally arranged up-right or upside down expansion strut pairs of chevron-configuration within the first, second or third expansion strut columns; the expansion strut pairs of chevron-configuration can be arranged in any tilted angulation within their assigned expansion columns. The first and second expansion struts of chevron-shape in a first expansion strut pair are parallel to each other, but the first and second expansion struts of chevron-shape in a first expansion strut pair do not parallel to the longitudinal axis of the tubular stent.

However, the first and second expansion struts of chevron-shape in a first expansion strut pair do not have to parallel to each other. Both the parallel and non-parallel arrangement of the first and second expansion struts of chevron-shape in a first expansion strut pair are within the scope of this invention. Furthermore, first and second expansion struts of chevron-shape in a first expansion strut pair can be made of dissimilar chevron patterns within a first expansion strut pair and within the same expansion strut column.

A first expansion strut pair first corner is formed where the first joining strut is coupled to the first expansion strut of chevron-shape, and a first expansion strut pair second corner is formed where the first joining strut is coupled to the second expansion strut of chevron-shape. A second expansion strut pair first corner is formed where the second joining strut is coupled to the second expansion strut of chevron-shape, and a second expansion strut pair second corner is formed where the second joining strut is coupled to the third expansion strut of chevron-shape. A third expansion strut pair first corner is formed where the third joining strut is coupled to the third expansion strut of chevron-shape, and a third expansion strut pair second corner is formed where the third joining strut is coupled to the fourth expansion strut of chevron-shape. A fourth expansion strut pair first corner is formed where the fourth joining strut is coupled to the fourth expansion strut of chevron-shape, and a fourth expansion strut pair second corner is formed where the fourth joining strut is coupled to the fifth expansion strut.

A second expansion column consists of a plurality of second expansion strut pairs of generally a chevron-shape in upside down position. A first expansion strut pair includes a first expansion strut of a chevron-shape, which has a stair-step configuration at the center and is dissimilar to a second expansion strut configuration, adjacent to a second expansion strut of a chevron-shape. A first joining strut couples the first and second expansion struts of chevron-shape at a proximal end of a first expansion strut pair to form a closed loop. When a first expansion strut pair is joined by a first joining strut to form a closed loop, a chevron-shaped slot is formed inside the first expansion strut pair, with a narrower slot width in the proximal half and a wider slot width in the distal half, due to the dissimilar chevron-shapes of the first and second first expansion struts of a first expansion strut pair. A second expansion strut pair includes a third expansion strut of chevron-shape, which has a stair-step configuration at the center and is dissimilar to a second expansion strut configuration, adjacent to the second expansion strut of chevron-shape. A second joining strut couples the second and third expansion struts at a distal end of the second expansion strut pair to form a closed loop. When a second expansion strut pair is joined by a second joining strut to form a closed loop, a chevron-shaped slot is formed inside the second expansion strut pair, with a narrower slot width in the distal half and a wider slot within the proximal half, due to the dissimilar chevron-shapes of the second and third expansion struts of a second expansion strut pair. A third expansion strut pair includes a fourth expansion strut of chevron-shape adjacent to the third expansion strut of chevron-shape, which has a stair-step configuration at the center and is dissimilar to a fourth expansion strut configuration. A third joining strut couples the third and fourth expansion struts at a proximal end of the third expansion strut pair to form a closed loop. When a third expansion strut pair is joined by a third joining strut to form a closed loop, a chevron-shaped slot is formed inside the third expansion strut pair, with a narrower slot width in the proximal half and a wider slot width in the distal half, due to the dissimilar chevron-shapes of the third and fourth expansion struts of a third expansion strut pair. A fourth expansion strut pair includes a fifth expansion strut of chevron-shape, which has a stair-step configuration at the center and is dissimilar to a fourth expansion strut configuration, adjacent to a fourth expansion strut of chevron-shape. A fourth joining strut couples the fourth and fifth expansion struts at a distal end of the fourth expansion strut pair. When a fourth expansion strut pair is joined by a fourth joining strut to form a closed loop, a chevron-shaped slot is formed inside the fourth expansion strut pair, with a narrower slot width in the distal half and a wider slot width in the proximal half, due to the dissimilar chevron-shapes of the fourth and fifth expansion struts of a fourth expansion strut pair. These expansion strut pairs of two dissimilar chevron-shape coupled by a joining struts to form a closed loop in an alternating proximal or distal end of the expansion strut pairs can be repeated to make the prescribed number of continues chain of expansion strut pairs in a first expansion column around the circumference in an unbroken fashion in a tubular stent of present invention. A set of two consecutive chevron-shaped expansion strut pairs in an unbroken sequence is called expansion strut cycles. In this application, the illustrations contain six (6) chevron-shaped expansion strut pair cycles or twelve (12) chevron-shaped expansion strut pairs in a second expansion column in the 2-dimensional cut-open drawings. However, the number of chevron-shaped expansion strut pairs or expansion strut pair cycles in a second expansion column can variably be changed according to the application requirements of the specific stent made of present invention. The variation of the number of expansion strut pairs or expansion pair cycles in a second expansion column is within the scope of a tubular stent of present invention.

Although the illustrations in this application shows only a neutrally arranged upright or upside down expansion strut pairs of chevron-configuration within the first, second or third expansion strut columns; the expansion strut pairs of chevron-shape can be arranged in any tilted angulation within their assigned expansion columns. The first and second expansion struts of chevron-shape in a first expansion strut pair in a second expansion column are parallel to each other, but the first and second expansion struts of chevron-shape in a first expansion strut pair in a second expansion column do not parallel to the longitudinal axis of the tubular stent. However, the first and second expansion struts of chevron-shape in a first expansion strut pair in a second expansion column do not have to parallel to each other. Both the parallel and non-parallel arrangement of the first and second expansion struts of chevron-shape in a first expansion strut pair in a second expansion column is within the scope of this invention. Furthermore, first and second expansion struts of chevron-shape in a first expansion strut pair in a second expansion column can be made of dissimilar chevron patterns as shown in the illustrations of this provisional application. However, the first and second expansion struts of chevron-shape in a first expansion strut pair in a second expansion column can be made of similar chevron-shapes; the first and second expansion struts in a first expansion strut pair may consists of two straight chevron-shape struts or the first and second expansion struts in a first expansion strut pair may consists of two stair-step chevron-shape struts.

A first expansion strut pair first corner is formed where the first joining strut is coupled to the first expansion strut of chevron-shape, and a first expansion strut pair second corner is formed where the first joining strut is coupled to the second expansion strut of chevron-shape. A second expansion strut pair first corner is formed where the second joining strut is coupled to the second expansion strut of chevron-shape, and a second expansion strut pair second corner is formed where the second joining strut is coupled to the third expansion strut of chevron-shape. A third expansion strut pair first corner is formed where the third joining strut is coupled to the third expansion strut of chevron-shape, and a third expansion strut pair second corner is formed where the third joining strut is coupled to the fourth expansion strut of chevron-shape. A fourth expansion strut pair first corner is formed where the fourth joining strut is coupled to the fourth expansion strut of chevron-shape, and a fourth expansion strut pair second corner is formed where the fourth joining strut is coupled to the fifth expansion strut.

A first connecting strut column is formed of a plurality of first connecting struts. Each first connecting strut in a first connecting strut column includes a connecting strut proximal section, a connecting strut distal section and a connecting strut intermediate section. A first connecting strut proximal section has two parts; a first short part that is coupled at a perpendicular or slant angle to the outer side of the distal end of a second expansion strut of first expansion strut pair in a first expansion column, and a second long part that is coupled to the first short part proximally and to the intermediate section distally. The second long part of first connecting strut proximal section generally parallels to the distal half of a second expansion strut of chevron-shape of first expansion strut pair in a first expansion column, although the second long part can be non-parallel to the distal half of a second expansion strut of chevron-shape of first expansion strut pair in a first expansion column, as an alternative configuration. A first connecting strut distal section also has two parts; a first short part that is coupled at a perpendicular or slant angle to the outer side of the proximal end of a first expansion strut of a first expansion strut pair in a second expansion column, and a second long part that is coupled to the first short part distally and to the intermediate section proximally. The second long part generally parallels to the proximal half of a first expansion strut of chevron-shape of a first expansion strut pair in a second expansion column, although the second long part can be non-parallel to the proximal half of a first expansion strut of chevron-shape of first expansion strut pair in a second expansion column, as an alternative configuration. A first connecting strut intermediate section proximal end is coupled at a slant angle to the distal end of first connecting strut proximal section long part and the first connecting strut intermediate section distal end is coupled at a slant angle to the proximal end of a first connecting strut distal section long part. The intermediate section of a first connecting strut traverses diagonally through the inter-connecting space between a first expansion strut pair closed loop in a first expansion strut column and a first expansion strut pair closed loop in a second expansion strut column. This diagonal course of the intermediate section of the first connecting strut is a key feature for contralaterally attaching the proximal and distal end of a first connecting strut to the opposite sides of the two apposed closed loop expansion strut pair in a first expansion column and a second expansion column. Because they attach to the opposite sides of the apposed closed loop expansion strut pairs in a first and second expansion column, the proximal and distal ends of a first connecting strut points to the opposite direction as they join with the respective attachment sites.

A third expansion column consists of a plurality of third expansion strut pairs of generally a chevron-shape in upright position. A first expansion strut pair includes a first expansion strut of a chevron-shape, which has a stair-step configuration at the center and is dissimilar to a second expansion strut configuration, adjacent to a second expansion strut of a chevron-shape. A first joining strut couples the first and second expansion struts of chevron-shape at a proximal end of a first expansion strut pair to form a closed loop. When a first expansion strut pair is joined by a first joining strut to form a closed loop, a chevron-shaped slot is formed inside the first expansion strut pair, with a narrower slot width in the proximal half and a wider slot width in the distal half, due to the dissimilar chevron-shapes of the first and second first expansion struts of a first expansion strut pair. A second expansion strut pair includes a third expansion strut of chevron-shape, which has a stair-step configuration at the center and is dissimilar to a second expansion strut configuration, adjacent to the second expansion strut of chevron-shape. A second joining strut couples the second and third expansion struts at a distal end of the second expansion strut pair to form a closed loop. When a second expansion strut pair is joined by a second joining strut to form a closed loop, a chevron-shaped slot is formed inside the second expansion strut pair, with a narrower slot width in the distal half and a wider slot width in the proximal half, due to the dissimilar chevron-shapes of the second and third expansion struts of a second expansion strut pair. A third expansion strut pair includes a fourth expansion strut of chevron-shape adjacent to the third expansion strut of chevron-shape, which has a stair-step configuration at the center and is dissimilar to a fourth expansion strut configuration. A third joining strut couples the third and fourth expansion struts at a proximal end of the third expansion strut pair to form a closed loop. When a third expansion strut pair is joined by a third joining strut to form a closed loop, a chevron-shaped slot is formed inside the third expansion strut pair, with a narrower slot width in the proximal half and a wider slot width in the distal half, due to the dissimilar chevron-shapes of the third and fourth expansion struts of a third expansion strut pair. A fourth expansion strut pair includes a fifth expansion strut of chevron-shape, which has a stair-step configuration at the center and is dissimilar to a fourth expansion strut configuration, adjacent to a fourth expansion strut of chevron-shape. A fourth joining strut couples the fourth and fifth expansion struts at a distal end of the fourth expansion strut pair. When a fourth expansion strut pair is joined by a fourth joining strut to form a closed loop, a chevron-shaped slot is formed inside the fourth expansion strut pair, with a narrower slot width in the distal half and a wider slot width in the proximal half, due to the dissimilar chevron-shapes of the fourth and fifth expansion struts of a fourth expansion strut pair. These expansion strut pairs of two dissimilar chevron-shape coupled by a joining struts to form a closed loop at an alternating proximal or distal end of the expansion strut pairs can be repeated to make the prescribed number of expansion strut pairs in an unbroken fashion around the circumference in a tubular stent of present invention. A set of two consecutive chevron-shaped expansion strut pairs in an unbroken sequence is called expansion strut cycles. In this application, the illustrations contain six (6) chevron-shaped expansion strut pair cycles or twelve (12) chevron-shaped expansion strut pairs in a third expansion column in the 2-dimensional cut-open drawings. However, the number of chevron-shaped expansion strut pairs or expansion strut pair cycles in a third expansion column can variably be changed according to the application requirements of the specific stent of present invention made. The variation of the number of expansion strut pairs or expansion strut pair cycles in a third expansion column is within the scope of a tubular stent of present invention.

Although the illustrations in this application shows only a neutrally arranged upright or upside down expansion strut pairs of chevron-configuration within the first, second or third expansion strut columns; the expansion strut pairs of chevron-shape can be arranged in any tilted angulation within their assigned expansion columns. The first and second expansion struts of chevron-shape in a first expansion strut pair in a second expansion column are parallel to each other, but the first and second expansion struts of chevron-shape in a first expansion strut pair in a second expansion column do not parallel to the longitudinal axis of the tubular stent. However, the first and second expansion struts of chevron-shape in a first expansion strut pair in a third expansion column do not have to parallel to each other. Both the parallel and non-parallel arrangement of the first and second expansion struts of chevron-shape in a first expansion strut pair in a third expansion column is within the scope of a tubular stent of present invention. Furthermore, first and second expansion struts of chevron-shape in a first expansion strut pair in a third expansion column can be made of dissimilar chevron patterns as shown in the illustrations of this provisional application. However, the first and second expansion struts of chevron-shape in a first expansion strut pair in a third expansion column can be made of similar chevron-shapes; the first and second expansion struts in a first expansion strut pair may consists of two straight chevron-shape struts or the first and second expansion struts in a first expansion strut pair may consists of two stair-step chevron-shape struts.

A first expansion strut pair first corner is formed where the first joining strut is coupled to the first expansion strut of chevron-shape, and a first expansion strut pair second corner is formed where the first joining strut is coupled to the second expansion strut of chevron-shape. A second expansion strut pair first corner is formed where the second joining strut is coupled to the second expansion strut of chevron-shaped, and a second expansion strut pair second corner is formed where the second joining strut is coupled to the third expansion strut of chevron-shape. A third expansion strut pair first corner is formed where the third joining strut is coupled to the third expansion strut of chevron-shape, and a third expansion strut pair second corner is formed where the third joining strut is coupled to the fourth expansion strut of chevron-shape. A fourth expansion strut pair first corner is formed where the fourth joining strut is coupled to the fourth expansion strut of chevron-shape, and a fourth expansion strut pair second corner is formed where the fourth joining strut is coupled to the fifth expansion strut.

A second connecting strut column is formed of a plurality of second connecting struts. Each first connecting strut in a second connecting strut column includes a connecting strut proximal section, a connecting strut distal section and a connecting strut intermediate section. A first connecting strut proximal section has two parts; a first short part that is coupled at a perpendicular or slant angle to the outer side of the distal end of a second expansion strut of first expansion strut pair in a second expansion column, and a second long part that is coupled to the first short part proximally and to the intermediate section distally. The second long part of first connecting strut proximal section generally parallels to the distal half of a second expansion strut of chevron-shape of second expansion strut pair in a second expansion column, although the second long part can be non-parallel to the distal half of a second expansion strut of chevron-shape of second expansion strut pair in a second expansion column, as an alternative configuration. A first connecting strut distal section also has two parts; a first short part that is coupled at a perpendicular or slant angle to the outer side of the proximal end of a second expansion strut of a first expansion strut pair in a third expansion column, and a second long part that is coupled to the first short part distally and to the intermediate section proximally. The second long part generally parallels to the proximal half of a second expansion strut of chevron-shape of a first expansion strut pair in a third expansion column, although the second long part can be non-parallel to the proximal half of a second expansion strut of chevron-shape of first expansion strut pair in a third expansion column, as an alternative configuration. A first connecting strut intermediate section proximal end is coupled at a slant angle to the distal end of first connecting strut proximal section long part and the first connecting strut intermediate section distal end is coupled at a slant angle to the proximal end of a first connecting strut distal section long part. The intermediate section of a second connecting strut traverses diagonally through the inter-connecting space between a first expansion strut pair closed loop in a second expansion column and a first expansion strut pair closed loop in a third expansion column. This diagonal course of the intermediate section of the first connecting strut is a key feature for contralaterally attaching the proximal and distal end of a second connecting strut to the opposite sides of the two apposed closed loop expansion strut pairs in a first expansion column and a second expansion column. Because they attach to the opposite sides of the apposed closed loop expansion strut pairs in a first and second expansion column, the proximal and distal ends of a second connecting strut points to the opposite directions as they join with the respective attachment sites.

DETAILED DESCRIPTION OF THE DRAWINGS

Figure 1:
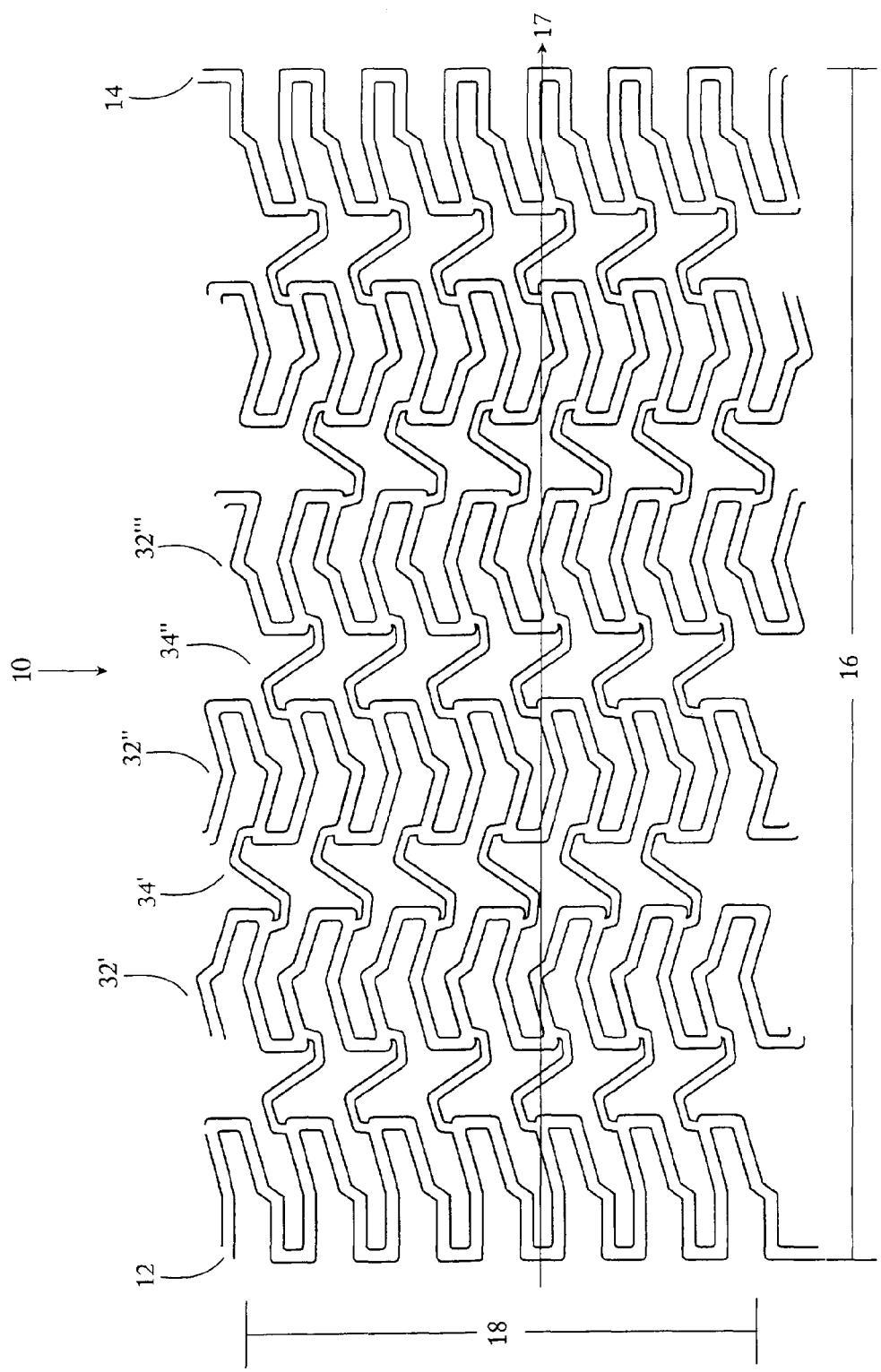
FIG. 1—A cut open 2-dimensional view of the strut pattern of stent 10 of present invention in an unexpanded state.

In the FIG. 1, The entire tubular stent 10 is laid out in a 2-dimensional drawing to illustrate the orientation of the stent 10 in an unexpanded state. The stent 10 has a continuous chain-mesh pattern formed of the expansion strut columns 32 and the connecting strut columns 34 between the expansion columns 32. The longitudinal axis 17 and the stent length 16 are arranged horizontally with the proximal end 12 on the left and the distal end 14 on the right.

Figure 2:
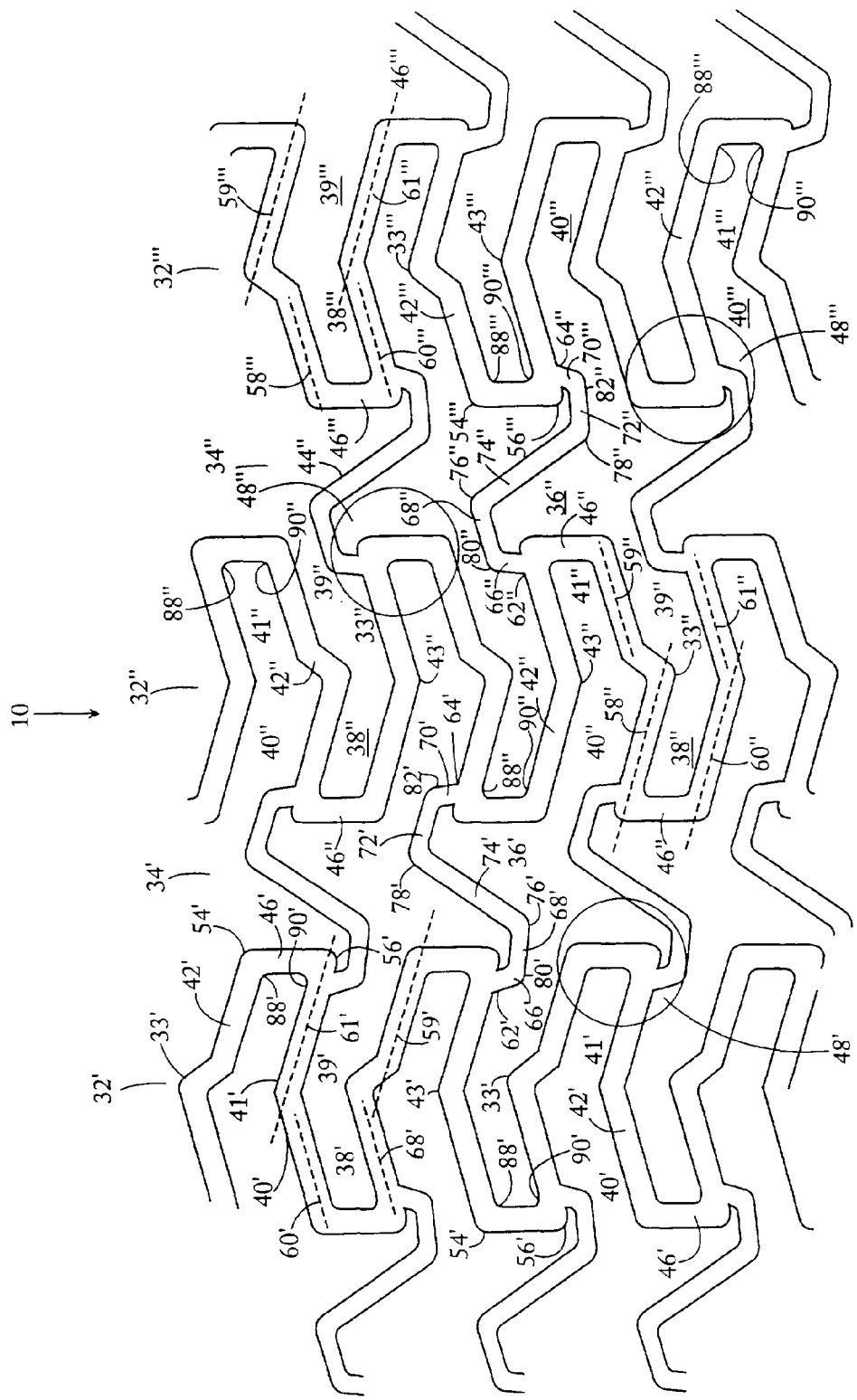
FIG. 2—A Magnified view of key area of the stent 10 shown in cut-open view to clearly mark the essential features of the stent 10; the expansion columns 32', 32", 32''', the connecting columns 34', 43", the chevron-shaped expansion struts 42', 42", 42''', the diagonal connecting struts 44', 44", the closed loop 48', 48", 48" expansion strut pairs, the stent cells 36', 36", the chevron shaped slot widths 38'-39', 38"-39", 38'''-38''' and 40'-41', 40"-41", 40'''-41'''.
Figure 3:
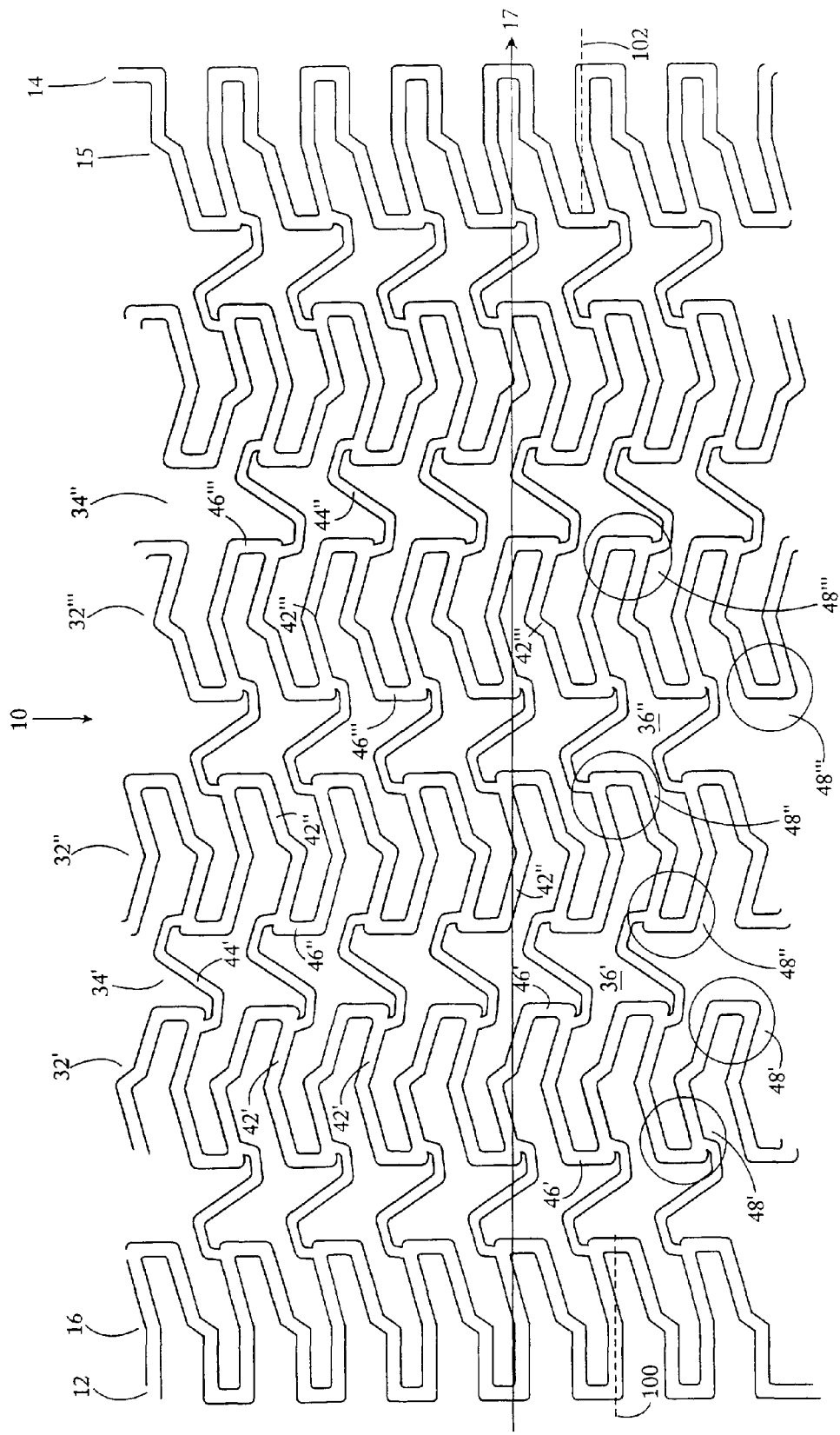
FIG. 3—An enlarged view of the stent 10 in its entirety in 2-dimensional cut open drawing in an unexpanded state to illustrate the arrangements of the expansion columns 32', 32", 32''', the connecting columns 44', 44', the proximal and distal end expansion rings 13, 15, and formation of stent cells 36', 36" around the circumference 18 and along the longitudinal axis 17 to construct the stent 10 in an unbroken chain-mesh pattern.

The FIG. 2 and FIG. 3 would be used intermingling through out the description of this application of a tubular stent 10.

To describe the design geometer of the stent 10 of present invention, only the 2-dimensional cut-open illustrations of the unexpanded stent 10 are used. Although description of strut frame configuration of the stent 10 is depicted in the 2-dimensional cut-open drawings, the stent 10 of present invention is a 3-dimensional tubular object designed to function as a scaffolding device when it is expanded inside a blood vessel, or inside an anatomic tubular structure of any kind in which the stent 10 can be implanted.

A first expansion column 32' includes of a plurality of first expansion strut 42' pairs of dissimilar chevron-shape in upright position. A first expansion strut pair includes a first expansion strut of a quasi-chevron shape, which has a stair-step or a "stepped bridge" configuration with a vertex or apex 33' at the center, which is dissimilar to the adjacent second expansion strut of generally a symmetrical chevron-shape with an apex or vertex 43' at the center. A first joining strut 46' couples the first and second expansion struts 42' of chevron or quasi-chevron shape at a distal end of a first expansion strut pair to form a closed loop 48'. When a first expansion strut 42' pair is joined by a first joining strut 46' to form a closed loop 48' at a distal end, a chevron-shaped or quasi-chevron shaped slot is formed inside the first expansion strut pair closed loop 48' with a proximal wide section 40' and a distal narrow section 41' of the slot, due to the dissimilar chevron-shapes of the first and second first expansion strut 42' pairs in a first expansion column 32'.

A second expansion strut pair includes a third expansion strut 42' of generally a quasi-chevron shape with a stair-step or "stepped bridge" configuration at the vertex or apex 33' at the center, which is dissimilar to the adjacent second expansion strut 42' of generally a symmetrical chevron-shape with a vertex or apex 43' at the center. A second joining strut 46' couples the second and third expansion struts 42' at a proximal end of a second expansion strut 42' pair to form a second closed loop 48'. When a second expansion strut 42' pair is joined by a joining strut 46' to form a second closed loop 48', a chevron shaped or quasi-chevron shaped slot is formed inside the second closed loop 48' with a proximal narrow section 38' and a distal wide section 39', due to the dissimilar chevron-shapes of the second and third expansion struts 42' of a second expansion strut 42' pair.

A third expansion strut pair includes a fourth expansion strut 42' of generally a symmetrical chevron-shape with a vertex or apex 43' at the center, adjacent to a third expansion strut 42' of a quasi-chevron shape, which has a stair-step or "stepped bridge" configuration with a vertex or apex 33' at the center. A third joining strut 46' couples the third and fourth expansion struts 42' at a distal end of a third expansion strut 42' pair to form a third closed loop 48'. When a third expansion strut pair is joined by a third joining strut 46' to form a closed loop 48', a chevron-shaped or quasi-chevron shaped slot is formed inside the third closed loop 48' with a proximal wide section 40' and a distal narrow section 41', due to the dissimilar chevron-shape configurations of the fourth and third expansion struts 42' of a third expansion strut pair.

A fourth expansion strut pair includes a fifth expansion strut 42' of a quasi-chevron shape with a stair-step or "stepped bridge" configuration with a vertex apex 33' at the center, adjacent to a fourth expansion strut 42' of a symmetrical chevron-shape with a vertex or apex 43' at the center. A fourth joining strut 46' couples the fourth and fifth expansion struts 42' at a proximal end of a fourth expansion strut pair to form a closed loop 48'. When a fourth expansion strut pair is joined by a fourth joining strut 46' to form a closed loop 48', a quasi-chevron shaped slot is formed inside the fourth expansion strut pair closed loop 48' with a proximal narrow section 38' and a distal wide section 39', due to dissimilar chevron-shapes of the fourth and fifth expansion struts 42' of a fourth expansion strut pair.

These expansion strut pairs of two dissimilar chevron-shapes coupled by a joining strut 46' to form a closed loop 48' in an alternating proximal or distal end of the expansion strut pairs can be repeated to make the prescribed number of continues chain of expansion strut pairs around the circumference in an unbroken fashion in the stent 10 of present invention. A set of two consecutive chevron-shaped expansion strut 42' pairs in an unbroken sequence is called expansion strut cycles. In this application, FIGS. 1 & 3 contain six (6) quasi-chevron shaped expansion strut cycles or twelve (12) chevron-shaped expansion strut pairs in a first expansion column 32' in the 2-dimensional cut-open drawings of the unexpanded stent 10 of present invention. However, the number of chevron-shaped expansion strut 42' pairs or expansion strut 42' cycles in a first expansion column 32' can variably be changed according to the application requirements of the specific stent 10 made of the present invention. Variation of the number of expansion strut pairs or expansion strut cycles in a first expansion column 32' is within the scope of a tubular stent 10 of present invention.

Although the illustrations in this application show only a neutrally arranged upright or upside down expansion strut 42' pairs of chevron-configuration within the first 32', second 32" or third 32''' expansion strut column; the expansion strut pairs of chevron-configuration can be arranged in any tilted angulation within their assigned expansion column 32. The first and second expansion struts 42' of dissimilar chevron-shape in a first expansion strut 42' pair in a first expansion column 32' are parallel to each other. The longitudinal axis 58' of proximal half section of the first expansion strut 42' is parallel to the longitudinal axis 60' of proximal half section of the second expansion strut 42', and the longitudinal axis 59' of distal half section of the first expansion strut 42' to the longitudinal axis 61' of distal half section of the second expansion strut 42'. However, the first and second expansion struts 42' of chevron-shape in a first expansion strut pair in the first expansion column 32' do not have to parallel to each other. But the first and second expansion struts 42' of chevron-shape in a first expansion strut pair do not parallel to the longitudinal axis 17 of the tubular stent 10. Both the parallel and non-parallel arrangement of the first and second expansion struts 42' of chevron-shape in a first expansion strut pair in a first expansion column 32' are within the scope of a tubular stent 10 of present invention. Furthermore, first and second expansion struts 42' of chevron-shape in a first expansion strut pair can be made of similar chevron pattern in a first expansion column 32'.

A first expansion strut pair first corner 54' is formed where the first joining strut 46' is coupled to the first expansion strut 42' and a first expansion strut pair second corner 56' is formed where the first joining strut 46' is coupled to the second expansion strut 42' in the first expansion column 32'. A second expansion strut pair first corner 54' is formed where the second joining strut 46' is coupled to the second expansion strut 42', and a second expansion strut pair second corner 56' is formed where the second joining strut 46' is coupled to the third expansion strut 42'. A third expansion strut pair first corner 54' is formed where the third joining strut 46' is coupled to the third expansion strut 42', and a third expansion strut pair second corner 56' is formed where the third joining strut 46' is coupled to the fourth expansion strut 42'. A fourth expansion strut pair first corner 54' is formed where the fourth joining strut 46' is coupled to the fourth expansion strut 42', and a fourth expansion strut pair second corner 56' is formed where the fourth joining strut 42' is coupled to the fifth expansion strut 42'. Likewise, any number of expansion strut pair are being joined by a respective joining strut 46' to form the first 54' and second 56' corners to form a prescribed number of continuous chain of expansion strut pairs in a tubular stent 10 of present invention.

A second expansion column 32" consists of a plurality of second expansion strut 42" pair of dissimilar chevron-shape in upside down position. A first expansion strut pair includes a first expansion strut 42" of a quasi-chevron shape, which has a stair-step or "stepped bridge" configuration with an upside down vertex or apex 33' at the center, adjacent to a second expansion strut 32" of a symmetrical chevron-shape with an upside down vertex or apex 43" at the center. A first joining strut 46" couples the first and second expansion struts 42" of dissimilar chevron-shape at a proximal end of a first expansion strut pair to form a closed loop 48". When a first expansion strut pair is joined by a first joining strut 46" to form a closed loop 48', a quasi-chevron shaped slot of an uneven width is formed inside the first expansion strut pair closed loop 48", with a proximal narrow section 38" and a distal wide section 39", due to the dissimilar chevron-shapes of the first and second expansion struts 42" of a first expansion strut pair. A second expansion strut pair includes a third expansion strut 32" of a quasi-chevron shape, which has a stair-step or "stepped bridge" configuration with a downward vertex or apex 33" at the center, adjacent to a second expansion strut 32" of a symmetrical chevron-shape with a downward vertex or apex 43" at the center. A second joining strut 46" couples the third and second expansion struts 42" of dissimilar chevron-shape at a distal end of a second expansion strut pair to form a closed loop 48". When a second expansion strut pair is joined by a second joining strut 46" to form a closed loop 48', a quasi-chevron shaped slot is formed inside the second expansion strut pair closed loop 48" with a proximal wide section 40" and a distal narrow section 41", due to the dissimilar chevron-shapes of the second and third expansion struts 42" of a second expansion strut pair.

A third expansion strut pair includes a fourth expansion strut 42" of a symmetrical chevron-shape with a downward vertex or apex 43" at the center, adjacent to a third expansion strut 42" of a quasi-chevron shape, which has a stair-step or "stepped bridge" configuration with a downward vertex or apex 33" at the center. A third joining strut 46" couples the third and fourth expansion struts 42" of dissimilar chevron-shape at a proximal end of a third expansion strut pair to form a closed loop 48". When a third expansion strut 42" pair is joined by a third joining strut 46" to form a closed loop 48", a quasi-chevron shaped slot is formed inside the third expansion strut pair closed loop 48" with a proximal narrow section 38" and a distal wide section 39", due to dissimilar chevron-shapes of the third and fourth expansion struts 42" of a third expansion strut pair.

A fourth expansion strut pair includes a fifth expansion strut 42" of a quasi-chevron shape, which has a stair-step or "stepped bridge" configuration with a downward vertex or apex 33" at the center, adjacent to a fourth expansion strut of generally a symmetrical chevron-shape with a downward vertex or apex 43" at the center. A fourth joining strut 46" couples the fourth and fifth expansion struts 42" at a distal end of a fourth expansion strut pair to form a closed loop 48". When a fourth expansion strut pair is joined by a fourth joining strut 46" to form a closed loop 48", an uneven quasi-chevron shaped slot is formed inside the fourth expansion strut pair closed loop 48" with a proximal wide section 40" and a distal narrow section 41", due to dissimilar chevron-shapes of the fourth and fifth expansion struts 42' of a fourth expansion strut pair.

These expansion strut pairs of two dissimilar chevron-shaped struts 42" coupled by a joining strut 46" to form a closed loop 48" in proximal or distal end of the expansion strut pairs in an alternating pattern can be repeated to make the prescribed number of continuous chain of expansion strut pairs around the circumference in an unbroken fashion in the stent 10 of present invention. A set of two consecutive dissimilar chevron-shaped expansion strut pairs in an unbroken sequence is called expansion strut cycles. In this application, a second expansion column 32" of FIGS. 1 & 2 contain six (6) chevron-shaped expansion strut pair cycles or twelve (12) chevron-shaped expansion strut 42" pairs in the 2-dimensional cut-open drawings of the unexpanded stent 10 of present invention. However, the number of chevron-shaped expansion strut pairs or expansion strut pair cycles in a second expansion column 32" can variably be changed according to the application requirements of the specific stent 10 made. Variation of the number of expansion strut pairs or expansion strut pair cycles in a second expansion column 32" is within the scope of a tubular stent 10 of present invention.

Although the illustrations in this application shows only a neutrally arranged, and non-parallel to the longitudinal axis 17 of the stent 10, upright or upside down expansion strut pairs of chevron-configuration within the first 32' or second 32" expansion strut columns; the expansion strut pairs of chevron-configuration can be arranged in any tilted angulation within their assigned expansion column 32. The first and second expansion struts 42" of dissimilar chevron-shape of a first expansion strut pair in a second expansion column 32" are parallel to each other; with the longitudinal axis 58" of proximal half section of the stair-step or "stepped bridge" chevron strut 42" to the longitudinal axis 60" of proximal half section of a symmetrical chevron shape strut 42", and the longitudinal axis 59" of distal half section of the stair-step or "stepped bridge" chevron strut 42" to the longitudinal axis 61" of distal half section of the symmetrical chevron strut 42" of the first expansion strut pair in the second expansion column 32". But the first and second expansion struts 42" of dissimilar chevron-shape in a second expansion column 32" do not parallel to the longitudinal axis 17 of the tubular stent 10. However, the first and second expansion struts 42" of dissimilar chevron-shape in a second expansion column 32" may not have to parallel to each other. Both the parallel and non-parallel arrangement of the first and second expansion struts 42" of dissimilar chevron-shape in a second expansion column 32" are within the scope of a tubular stent 10 of present invention. Furthermore, first and second expansion struts 42" of dissimilar chevron-shape in an expansion strut pair in a second expansion column 32" can be made of similar chevron patterns within a second expansion column 32". The proximal section 58' of the first expansion strut 42' of a first expansion strut pair in a first expansion column 32' is parallel to the distal section 59" of a first expansion strut 42" of a first expansion strut pair in the second expansion column 32". The second section 59' of a first expansion strut 42' of a first expansion strut pair in a first expansion column 32' parallels to a first section 58" of a first expansion strut 42' of a first expansion strut pair in a second expansion column 32". The proximal section 60' of the first expansion strut 42' of a first expansion strut pair in a first expansion column 32' is parallel to the distal section 61" of a first expansion strut 42" of a first expansion strut pair in the second expansion column 32". The second section 61' of a first expansion strut 42' of a first expansion strut pair in a first expansion column 32' parallels to a first section 60" of a first expansion strut 42' of a first expansion strut pair in a second expansion column 32". Although in FIG. 2 & FIG. 3, certain sections of first strut pair in the first expansion column 32' parallels to a corresponding certain sections of first strut pair in the second expansion column 32", these respective sections in a first expansion column 32' and second expansion column 32" do not have to parallel to each other. This parallel or non-parallel variation of the sections of expansion struts 42' in a first expansion column 32' and the sections of expansion struts 42" in a second expansion column 32" is within the scope of stent 10 of present invention.

In the second expansion column 32", a first expansion strut pair first corner 54" is formed where the first joining strut 46" is coupled to the first expansion strut 42", and a first expansion strut pair second corner 56" is formed where the first joining strut 46" is coupled to the second expansion strut 42". A second expansion strut pair first corner 54" is formed where the second joining strut 46" is coupled to the second expansion strut 42", and a second expansion strut 42" pair second corner 56" is formed where the second joining strut 46" is coupled to the third expansion strut 42". A third expansion strut pair first corner 54" is formed where the third joining strut 46" is coupled to the third expansion strut 42", and a third expansion strut pair second corner 56" is formed where the third joining strut 46" is coupled to the fourth expansion strut 42". A fourth expansion strut pair first corner 54" is formed where the fourth joining strut 46" is coupled to the fourth expansion strut 42", and a fourth expansion strut pair second corner 56" is formed where the fourth joining strut 46" is coupled to the fifth expansion strut 42". Likewise, a number of expansion strut pair being formed by a joining strut 46" to form the first 54" and second 56" corners in the expansion strut pair in the second expansion column 32" can continue until a prescribed number of expansion strut pairs or cycles is reached in a stent 10 of present invention.

A first connecting strut column 34' is formed of a plurality of first connecting struts 44'. Each first connecting strut 44' in a first connecting strut column 34' includes a connecting strut proximal section, a connecting strut distal section and a connecting strut intermediate section 74'. A first connecting strut proximal section has two parts; a first short part or a "stem" 66' that is coupled at a perpendicular or slant angle to the outer side of the distal end of a second expansion 42' strut of first expansion strut pair in a first expansion column 32', and a second long part 68' that is coupled to the "stem" 66' proximally and to the intermediate section 74' distally. The second long part 68' of first connecting strut 44' proximal section generally parallels to the distal half section of a second expansion strut 42' of chevron-shape of first expansion strut pair in a first expansion column 32', although the second long part 68' can be non-parallel to the distal half section of a second expansion strut 42' of chevron-shape of first expansion strut pair in a first expansion column 32', as an alternative configuration. A first connecting strut 44' distal section also has two parts: a first short part or "stem" 70' that is coupled at a perpendicular or slant angle to the outer side of the proximal end of a first expansion strut 42' of a first expansion strut pair in a second expansion column 32", and a second long part 72' that is coupled to the first short part or stem 70' distally and to the intermediate section 74' proximally. The second long part 72' generally parallels to the proximal half section of a first expansion strut 42' of quasi-chevron shape of a first expansion strut pair in a second expansion column 32", although the second long part 72' can be non-parallel to the proximal half section of a first expansion strut 42" of quasi-chevron shape of first expansion strut pair in a second expansion column 32", as an alternative configuration. A first connecting strut 44' intermediate section 74' proximal end is coupled at a slant angle to the distal end of first connecting strut 44' proximal section long part 68' in a junction 76', and the first connecting strut 44' intermediate section 74' distal end is coupled at a slant angle to the proximal end of a first connecting strut distal section long part 72' at a junction 78'. The intermediate section 74' of a first connecting strut 44' traverses diagonally through the inter-connecting space between a first expansion strut pair closed loop 48' in a first expansion column 32' and a first expansion strut pair closed loop 48" in a second expansion column 32". This diagonal course of the intermediate section 74' of the first connecting strut 44' is a key feature for contralaterally attaching the proximal end 62' and distal end 64' of a first connecting strut 44' to the opposite sides (or Contralateral sides) of the two apposed closed loops 48', 48" respectively; between a closed loop 48' in a first expansion column 32' and a closed loop 48" in a second expansion column 32". Because they attach to the opposite sides of the apposed closed loops 48', 48" respectively in a first 32' and a second 32" expansion column, the proximal end 62' with its stem 66' and distal end 64' with its stem 70' of a first connecting strut 44' points to the opposite directions as they join to the respective attachment sites. There are six (6) connecting struts 44' in the first connecting column 34'. Each of these six (6) connecting strut 44' attaches to their respective attachment sites in the first 32' and second 32" expansion columns like the first connecting strut 44' described above, in an unbroken fashion around the circumference 18 of the stent 10, to form a tubular structure consists of a first expansion column 32', a first connecting column 34, and a second expansion column 32" with a longitudinal axis 17. When an unbroken tubular stent 10 is formed by a first expansion column 32', second expansion column 32" and a first connecting column 34', there are six (6) asymmetrical stent cells 36' formed in the tubular structure. In each of the stent cell 36', there are two quasi-chevron shape slots; a proximal slot in the proximal end and a distal slot in the distal end. The quasi-chevron shaped slots have a narrower proximal part 38' and wider distal part 39' in the proximal slot, and a wider proximal part 40" and narrower distal part 41' in the distal slot.

A third expansion column 32''' includes of a plurality of first expansion strut 42''' pairs of dissimilar chevron-shape in upright position. A first expansion strut pair includes a first expansion strut 42''' of a quasi-chevron shape, which has a stair-step or "stepped bridge" configuration with a vertex or apex 33''' at the center, adjacent to a second expansion strut 42''' of a symmetrical chevron-shape with a vertex or apex 43''' at the center. A first joining strut 46''' couples the first and second expansion struts 42''' at a proximal end of a first expansion strut pair to form a first closed loop 48'''. When a first expansion strut pair is joined by a first joining strut 46''' to form a closed loop 48''', a quasi-chevron shaped slot is formed inside the first expansion strut pair closed loop 48''' with a proximal narrow section 38''' and a distal wide section 39 ''', due to a dissimilar chevron-shapes of the first and second expansion struts 42''' in a third expansion column 32'''. A second expansion strut pair includes a third expansion strut of a quasi-chevron shape, which has a stair-step or "stepped bridge" configuration with a vertex or apex 33' at the center, adjacent to a second expansion strut 42''' of a symmetrical chevron-shape with a vertex or apex 43''' at the center. A second joining strut 46''' couples the third and second expansion struts 42''' of dissimilar chevron-shape at a distal end of a second expansion strut pair to form a closed loop 48'''. When a second expansion strut 42''' pair is joined by a first joining strut 46''' to form a closed loop 48''', a quasi-chevron shaped slot is formed inside the second expansion strut pair closed loop 48''' with a proximal wider section 40''' and a distal narrower section 41''', due to the dissimilar chevron-shapes of the second and third expansion struts 42''' of a second expansion strut pair. A third expansion strut pair includes a fourth expansion strut 42''' of a symmetrical chevron-shape with a vertex or apex 43''' at the center, adjacent to a third expansion strut 42''' of a quasi-chevron shape, which has a stair-step or "stepped bridge" configuration with a vertex or apex 33''' at the center. A third joining strut 46''' couples the third and fourth expansion struts 42''' of dissimilar chevron-shapes at a proximal end of a third expansion strut pair to form a closed loop 48'''. When a third expansion strut pair is joined by a third joining strut 46''' to form a closed loop 48''', a quasi-chevron shaped slot is formed inside the third expansion strut pair closed loop 48''' with a proximal narrower section 38''' and a distal wider section 39''', due to the dissimilar chevron-shape configurations of the fourth and third expansion struts 42'''. A fourth expansion strut pair includes a fifth expansion strut 42''' of a quasi-chevron shape, which has a stair-step or "stepped bridge" configuration with a vertex or apex 33''' at the center, adjacent to a fourth expansion strut of a symmetrical chevron-shape with a vertex or apex 43''' at the center. A fourth joining strut 46''' couples the fourth and fifth expansion struts 42''' of dissimilar chevron-shape at a distal end of a fourth expansion strut pair to form a closed loop 48'''. When a fourth expansion strut pair is joined by a fourth joining strut 46''' to form a closed loop 48''', a quasi-chevron shaped slot is formed inside the fourth expansion strut pair closed loop 48''' with a proximal wider section 40''' and a distal narrower section 41''', due to the dissimilar chevron-shapes of the fourth and fifth expansion struts 42''' of a fourth expansion strut pair.

These expansion strut pairs of two dissimilar chevron-shapes coupled by a joining strut 46''' to form a closed loop 48''' in an alternating proximal or distal end of the expansion strut pairs can be repeated to make the prescribed number of continues chain of expansion strut pairs around the circumference 18 in an unbroken fashion in the stent 10 of present invention. A set of two consecutive chevron-shaped expansion strut pairs in opposite directions in an unbroken sequence is called expansion strut cycles. In this application, FIGS. 1 & 3 contain six (6) chevron-shaped expansion strut pair cycles or twelve (12) chevron-shaped expansion strut pairs in a third expansion column 32''' in the 2-dimensional cut-open drawings of the unexpanded stent 10 of present invention. However, the number of chevron-shaped expansion strut pairs or expansion strut pair cycles in a third expansion column 32' can variably be changed according to the application requirements of the specific stent 10 made. Variation in the number of expansion strut pair or expansion strut pair cycle in a third expansion column 32''' is within the scope of a tubular stent 10 of present invention.

Although the illustrations in this application shows only a neutrally arranged upright expansion strut pairs of chevron-configuration within the third 32''' expansion strut column, the expansion strut pairs of chevron-configuration can be arranged in any tilted angulation within the third expansion column 32'''. The first and second expansion struts 42''' of dissimilar chevron-shape in a first expansion strut pair in a third expansion column 32''' are parallel to each other; with the longitudinal axis 58''' of proximal half section of the stair-step or "stepped bridge" chevron strut 42''' to the longitudinal axis 60''' of proximal half section of the symmetrical chevron strut 42''', and the longitudinal axis 59''' of distal half section of the stair-step chevron strut 42''' to the longitudinal axis 61''' of distal half section of the symmetrical chevron strut 42'''. But the first and second expansion struts 42''' of dissimilar chevron-shape in a first expansion strut pair do not parallel to the longitudinal axis 17 of the tubular stent 10. However, the first and second expansion struts 42''' of dissimilar chevron-shape in a first expansion strut pair in a third expansion column 32''' do not have to parallel to each other. Both the parallel and non-parallel arrangement of the first and second expansion struts 42''' of chevron-shape in a first expansion strut pair in a third expansion column 32''' are within the scope of a tubular stent 10 of present invention. Furthermore, first and second expansion struts 42''' of chevron-shape in a first expansion strut pair can be made of similar chevron patterns in a third expansion column 32''' The proximal section 58" of the first expansion strut 42" of a first expansion strut pair in a second expansion column 32" is parallel to the distal section 59''' of a first expansion strut 42''' of a first expansion strut pair in the third expansion column 32'''. The second section 59" of a first expansion strut 42" of a first expansion strut pair in a second expansion column 32' parallels to a first section 58''' of a first expansion strut 42''' of a first expansion strut pair in a third expansion column 32'''. The proximal section 60" of the first expansion strut 42" of a first expansion strut pair in a second expansion column 32" is parallel to the distal section 61''' of a first expansion strut 42''' of a first expansion strut pair in the third expansion column 32". The second section 61" of a first expansion strut 42" of a first expansion strut pair in a second expansion column 32" parallels to a first section 60''' of a first expansion strut 42''' of a first expansion strut pair in a third expansion column 32'''. Although in FIG. 2 & FIG. 3, certain sections of first strut pair in the second expansion column 32" parallels to a corresponding certain sections of first strut pair in the third expansion column 32''', these respective sections in a second expansion column 32" and third expansion column 32''' do not have to parallel to each other. This parallel or non-parallel variation of the sections of expansion struts 42" in a second expansion column 32" and the sections of expansion struts 42''' in a third expansion column 32''' is within the scope of stent 10 of present invention.

In the third expansion column 32''', a first expansion strut pair first corner 54''' is formed where the first joining strut 46''' is coupled to the first expansion strut 42''', and a first expansion strut pair second corner 56''' is formed where the first joining strut 46''' is coupled to the second expansion strut 42'''. A second expansion strut pair first corner 54''' is formed where the second joining strut 46''' is coupled to the second expansion strut 42''', and a second expansion strut pair second corner 56''' is formed where the second joining strut 46''' is coupled to the third expansion strut 42'''. A third expansion strut pair first corner 54''' is formed where the third joining strut 46''' is coupled to the third expansion strut 42''', and a third expansion strut pair second corner 56''' is formed where the third joining strut 46''' is coupled to the fourth expansion strut 42'''. A fourth expansion strut pair first corner 54''' is formed where the fourth joining strut 46''' is coupled to the fourth expansion strut 42''', and a fourth expansion strut pair second corner 56''' is formed where the fourth joining strut 42''' is coupled to the fifth expansion strut 42'''. Likewise, a series of expansion strut pair are being joined by a respective joining strut 46''' to form the first 54''' and second 56''' corners until a prescribed set of joined expansion strut pairs is reached to form a stent 10 of present invention.

A second connecting strut column 34" is formed of a plurality of second connecting struts 44". Each second connecting strut 44" in a second connecting strut column 34" includes a connecting strut proximal section, a connecting strut distal section and a connecting strut intermediate section 74". A first connecting strut proximal section has two parts; a first short part or stem 66" that is coupled at a perpendicular or slant angle to the outer side of the distal end of a second expansion strut 42" of second expansion strut pair in a second expansion column 32", and a second long part 68" that is coupled to the first short part 66" proximally and to the intermediate section 74' distally. The second long part 68" of first connecting strut 44" proximal section generally parallels to the distal half section of a second expansion strut 42" of chevron-shape of first expansion strut pair in a second expansion column 32", although the second long part 68" can be made non-parallel to the distal half section of a second expansion strut 42" of chevron-shape of first expansion strut pair in a second expansion column 32", as an alternative configuration. A first connecting strut 44" distal section also has two parts; a first short part or stem 70" that is coupled at a perpendicular or slant angle to the outer side of the proximal end of a second expansion strut 42" of chevron-shape of a first expansion strut pair in a third expansion column 32'", and a second long part 72" that is coupled to the first short part 70" distally and to the intermediate section 74" proximally. The second long part 72" generally parallels to the proximal half of a second expansion strut 42'" of chevron-shape of a first expansion strut pair in a third expansion column 32'", although the second long part 72" can be made non-parallel to the proximal half of a second expansion strut 42'" of chevron-shape of a first expansion strut pair in a third expansion column 32'", as an alternative configuration. A first connecting strut 44" intermediate section 74" proximal end is coupled at a slant angle to the distal end of first connecting strut 44" proximal section long part 68" at a junction 76", and the first connecting strut 44" intermediate section 74" distal end is coupled at a slant angle to the proximal end of a first connecting strut distal section long part 72" at a junction 78". The intermediate section 74" of a first connecting strut 44" traverses diagonally through the inter-connecting space between a second expansion strut pair closed loop 48" in a second expansion column 32" and a first expansion strut pair closed loop 48'" in a third expansion column 32'". This diagonal course of the intermediate section 74" of the first connecting strut 44" is a key feature for contralaterally attaching the proximal end 62" and distal end 64" of a first connecting strut 44" to the opposite or contralateral sides of the two apposed closed loop 48", 48'" respectively in a second expansion column 32" and a third expansion column 32'". Because they attach to the opposite sides of the two apposed closed loops 48", 48'" in a second 32" and third 32'" expansion columns respectively, the proximal end 62" and distal end 64" of a first connecting strut 44" point to the opposite directions as they join to the respective attachment sites.

The vertical orientation of the second connecting struts 44" in a second connecting column 34" is 180 degrees upside down (or a mirror image) in comparison to the vertical orientation of the first connecting struts 44' in a first connecting column 34'. This alternating mirror image orientation of the connecting struts 44', 44" in two adjacent connecting strut columns 34', 34" continues as the length of a tubular stent 10 is added longitudinally. This alternating vertical orientation of the connecting struts 44 in adjacent connecting columns 34 is designed to prevent axial warping of the stent 10 during the process of passive expansion by a high pressure expansion balloon.

There are six (6) connecting struts 44" in the second connecting column 34". Each of these six (6) connecting strut 44" attaches to their respective attachment sites in the second expansion column 32" proximally and in the third 32'" expansion column distally, like the first connecting strut 44' described above in an unbroken fashion around the circumference 18 of the stent 10, to form a tubular structure. When an unbroken tubular stent structure 10 is formed by a second 32" and third 32'" expansion columns and a second connecting column 34", six (6) asymmetrical stent cells 36" are defined in the stent 10. Each stent cell 36" has quasi-chevron shaped slots at the proximal end and at the distal end. Each cell 36" has a narrower proximal section 38" and wider distal section 39'" in the proximal slot, and a wider proximal section 40'" and narrower distal section 41'" in the distal slot.

Figure 4:
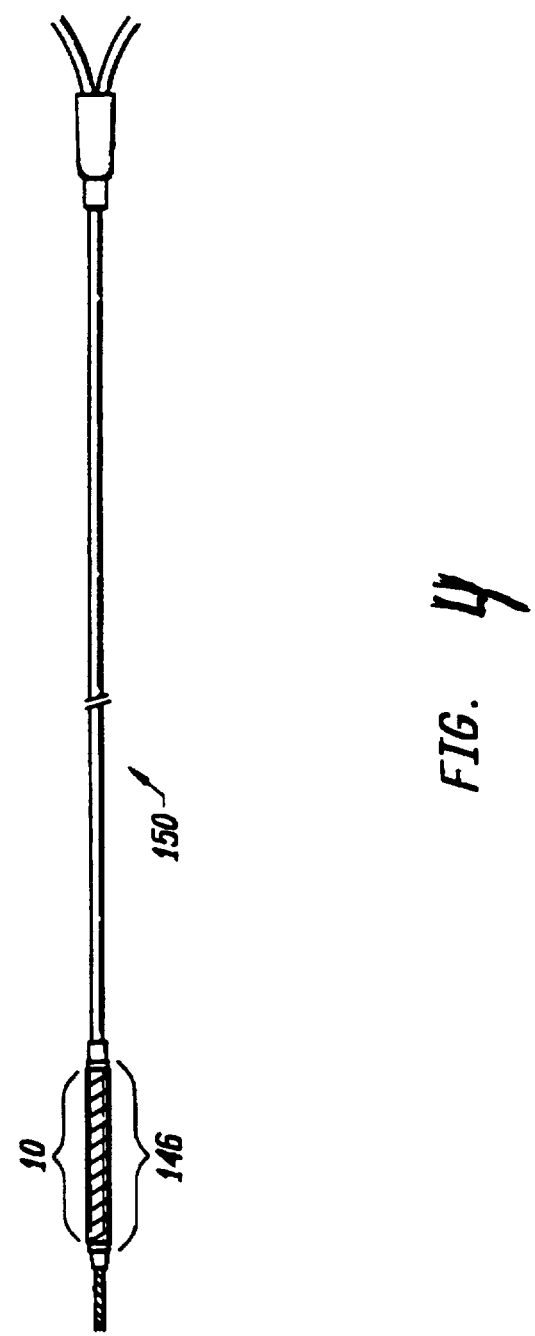
FIG. 4—A view of a delivery balloon catheter.

FIG. 4 shows a delivery balloon catheter generally at 150 with stent 10 disposed about balloon 146.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

I claim:

1. A medical device comprising:
   a radially expandable stent comprising
      a hollow, cylindrical body comprising first and second rings extending circumferentially around the cylindrical body, each ring comprising an undulating series of peaks and valleys formed by struts connecting alternating curved peak and valley segments within the ring, the struts comprising a first curved segment curved substantially symmetrically about a single circumference of the stent such that the peaks and valleys within a ring form a nested chevron pattern; and
   a plurality of longitudinal connections between the first and second rings,
   wherein each of the peaks and valleys have sides,
   wherein one of the plurality of longitudinal connections is attached to a side of a first peak in the first ring and to a contralateral side of a first valley in the second ring;
   wherein the first and second rings are arranged in an anti-parallel chevron pattern relative to each other.

2. The medical device of claim 1 wherein the struts further comprise a second curved segment positioned near a curved peak or valley segment.

3. The medical device of claim 1 wherein the peaks of the first ring are not longitudinally aligned with the valleys of the second ring.

4. The medical device of claim 3 wherein the peaks of the first ring are longitudinally aligned with the peaks of the second ring.

5. The medical device of claim 1 wherein at least one longitudinal connection is formed by a longitudinal connector.

6. The medical device of claim 5 wherein at least one longitudinal connector is curved.

7. The medical device of claim 5 wherein at least one longitudinal connector is straight.

8. The medical device of claim 1 further comprising at least one radiopaque marker.

9. The medical device of claim 1 wherein the radially expandable stent is a balloon-expandable stent.

10. The medical device of claim 1 wherein the radially expandable stent is a self-expanding stent.

11. The stent of claim 1,
    wherein the struts of each ring form a plurality of strut pairs,
    wherein one strut of a strut pair is chevron-shaped and the other strut of the strut pair has a stair-step configuration,
    wherein each of the plurality of longitudinal connections has a first end and a second end, and
    wherein the first end of one of the plurality of longitudinal connections is attached to a chevron-shaped strut in the first ring and the second end of the longitudinal connection is attached to a strut comprising a stair-step configuration in the second ring.

12. The stent of claim 1, wherein the plurality of longitudinal connections between the first and second rings are S-shaped.

13. The stent of claim 12,
wherein the cylindrical body further comprises a third ring extending circumferentially around the cylindrical body, the third ring comprising an undulating series of peaks and valleys formed by struts connecting alternating curved peak and valley segments within the third ring, the struts comprising a third curved segment curved substantially symmetrically about a single circumference of the stent such that the peaks and valleys within the third ring form a nested chevron pattern,
wherein the stent further comprises a plurality of longitudinal connections between the second and third rings,
wherein the struts of the third ring form a plurality of strut pairs,
wherein one strut of a strut pair of the third ring is chevron-shaped,
wherein each of the plurality of longitudinal connections between the second ring and the third ring has a first end and a second end, and
wherein the first end of one of the plurality of longitudinal connections between the second ring and the third ring is attached to a chevron-shaped strut in the second ring and the second end of the longitudinal connection between the second ring and the third ring is attached to a strut comprising a chevron-shaped strut in the third ring.

14. The stent of claim 13, wherein the plurality of longitudinal connections between the second ring and third ring are mirror images of the S-shaped longitudinal connections between the first and second rings taken along a circumferential axis.

* * * * *